(12) United States Patent
Neilesh

(10) Patent No.: US 8,548,839 B2
(45) Date of Patent: Oct. 1, 2013

(54) SYSTEM AND METHOD FOR FACILITATING HEALTHCARE VOLUNTEERING

(75) Inventor: Patel Neilesh, Los Altos, CA (US)

(73) Assignee: Healthcare Volunteer, Inc., Los Altos, CA (US)

( * ) Notice: Subject to any disclaimer, the term of this patent is extended or adjusted under 35 U.S.C. 154(b) by 90 days.

(21) Appl. No.: 12/945,569

(22) Filed: Nov. 12, 2010

(65) Prior Publication Data

US 2012/0123789 A1    May 17, 2012

(51) Int. Cl.
*G06Q 10/00* (2012.01)
(52) U.S. Cl.
USPC .......................... 705/7.13; 705/7.17; 705/7.23
(58) Field of Classification Search
USPC ......................................................... 705/2–8
See application file for complete search history.

(56) References Cited

U.S. PATENT DOCUMENTS

| | | | |
|---|---|---|---|
| 6,574,561 B2 * | 6/2003 | Alexander et al. ................ 702/5 |
| 2008/0059268 A1 * | 3/2008 | Davantes et al. .................. 705/8 |
| 2008/0133300 A1 * | 6/2008 | Jalinous ........................... 705/7 |
| 2009/0045942 A1 * | 2/2009 | Schurter ................. 340/539.11 |

* cited by examiner

*Primary Examiner* — Joseph Burgess
(74) *Attorney, Agent, or Firm* — Goodwin Procter LLP

(57) ABSTRACT

Computer-implemented methods and systems for connecting and facilitating communication among healthcare volunteers, organizations, patients and donors are disclosed. A matching system to match volunteers, donors, organizations and patients to coordinate and manage providing low cost or free health care services is disclosed. An donation inventory management system is also disclosed. Dynamic volunteer coordination methods for responding to public health events are also disclosed.

5 Claims, 17 Drawing Sheets

SYSTEM AND METHOD FOR FACILITATING HEALTHCARE VOLUNTEERING

BACKGROUND

Healthcare organizations such as non-governmental organizations (NGOs) (e.g. The Red Cross) and hospitals constantly seek out volunteers, financial donors and in-kind donors to support their charitable healthcare operations around the world. Typically cash-conscious non-profit organizations, these healthcare organizations are confronted by the logistical and operational burdens of continuously staffing, provisioning and funding their various efforts to provide healthcare services to underserved regions domestically and internationally. The continuous process of managing multiple healthcare projects requires substantial overhead that diverts time and financial resources away from being applied directly towards providing care to those in need.

Despite the recent explosion of online portals and social networking applications, conventional websites are generally inadequate to serve the needs of the volunteer healthcare community, especially the unique needs of healthcare organizations. For one, given the variety of hidden healthcare needs to be addressed over a wide geographical scope, healthcare organizations cannot rely on postings to attract sufficient volunteers or funding. Even if they have been able to secure sufficient funding, equipment or supplies for projects, NGOs often have a difficult time finding a sufficient number of skilled volunteers to staff their projects. Even after recruiting a sufficient team of volunteers for their projects, managing and organizing the team becomes a daunting and highly inefficient task. Conventional approaches that merely rely on project postings seeking volunteers (like a job posting) do not typically result in a sufficient number or level of volunteers responding to those posts. Those volunteers who are motivated to volunteer often find it difficult to create and manage the logistics of a volunteering opportunity, including raising funds, managing necessary licensing and arranging travel and supplies. Furthermore, patients who are either uninsured or underinsured find it difficult to find safety net providers, volunteer providers, county hospitals and federally qualified health centers (FQHCs) to provide them with the necessary treatment at a reduced or no cost. Donors, in turn, are often frustrated as it is difficult to view or monitor the use of their cash and in-kind donations, especially during natural disaster response scenarios, when a large amount of donations are received in a short amount of time.

The shortcomings of coordinating providing effective healthcare services using volunteers are especially evident in public health events such as natural or man-made disasters. In addition to problems relating to unreliable or compromised voice and data communications, there are also recurrent problems in coordinating the even and adequate staffing of hospitals, triage centers and other volunteer receiving areas around a disaster scene. This lack of coordination results in an unpredictable and uneven ability to care for disaster victims.

For at least the above reasons, conventional approaches to online communities and social networking still fall short of the special needs required in the context of connecting healthcare volunteers, financial and in-kind donors and healthcare organizations. In view of these limitations of the conventional art, systems and methods for facilitating improved communication and coordination among healthcare volunteers, donors, patients and healthcare organizations are desirable.

SUMMARY

Systems and methods facilitating improved communication and coordination among healthcare volunteers, government agencies, donors, patients, case workers and healthcare organizations are disclosed. In one aspect, the invention provides computer-implemented methods for connecting and facilitating communication between at least one donor (for example, a healthcare volunteer, a non-profit organization, a healthcare product company or a financial sponsor) and at least one healthcare requester (such as a patient, a healthcare volunteer, a non-profit organization, case worker, a healthcare company or a financial sponsor). The method includes receiving, using a network-connected receiver, an inquiry from a healthcare requester including a request for at least one service and/or product. A processor compares the received inquiry to at least one entry stored in an inventory database. Each entry includes a description of at least one service and/or product offered by a donor, and a corresponding availability parameter. For example, the description can correspond to a product and include a condition status, an ID number, a value, a device history, a specialty, dimensions; a picture and/or a manual, product/service physical description with one or more availability parameters optionally indicating immediate availability, no availability, pending availability, availability at a date, availability until a date, availability method (i.e. will ship, pick up in person, COD), transit time for shipment, a quantity and/or a current storage location (pick-up location).

A network-connected transmitter transmits a list reflecting the comparison of the received inquiry against the one or more entries stored in the inventory database, including at least one matching entry. A network-connected receiver receives a request from the healthcare requester corresponding to a matching entry, and the request is relayed to the donor associated with the matching entry. By facilitating queries of donor inventory databases, the present invention connects disparate resources and needs with increased efficiency. Furthermore, the ability to query inventory databases corresponding to each of a plurality of donors in various locations permits a distributed system of interactions and product shipping, avoiding the costs and inefficiencies of more centralized systems.

In certain embodiments, the method also includes receiving, using the network-connected receiver, an update file corresponding to a change in the inventory database. The update file is optionally received on a predetermined schedule to update the inventory database. The update file can either be pushed to or pulled into the system to be read by the inventory database. For example, the file or files can take the form of an xml feed, rss or other structured format reflecting current inventory data. In some embodiments, the method also includes storing the inquiry in a memory as a pending inquiry, comparing the at least one entry stored in the inventory database to the stored pending inquiry, and transmitting a notification to the healthcare recipient reflecting the comparison of the stored inquiry against the at least one entry stored in the inventory database. In various embodiments, the method also includes receiving an approval from the donor corresponding to the healthcare requester's request and generating shipping information based on the request, the matching entry, a healthcare recipient profile and a donor profile.

In another aspect, the invention provides a computer-implemented method for connecting and facilitating communication between a healthcare volunteer and a healthcare organization. The method includes storing, in a memory, a volunteer profile including general volunteer information and a healthcare organization profile including at least one project profile including at least one custom query and a corresponding custom answer. A network-connected receiver receives a request for an application form corresponding to a selected project profile. The at least one custom criterion associated with the selected project profile is transmitted and a completed volunteer application form is received. The completed volunteer application form includes a custom response for each custom criterion. Using a processor, the stored general volunteer information and the completed volunteer application form are evaluated, including by comparing the received custom response against the stored custom answer to identify a potential match. A notification of the potential match is transmitted to the healthcare organization and/or the volunteer.

In some embodiments, the method also includes generating a request for validation based on a stored volunteer profile and transmitting the request for validation to an independent organization, such as an automated directory of licensed medical practitioners.

In one embodiment, the method also includes storing, in a memory, volunteer application information that optionally includes a recommendation from a third party, an image of a government credential, and/or proof of insurance. In this embodiment, the method also includes transmitting a secure link to the organization corresponding to the stored volunteer application information; receiving a request from the organization corresponding to the link; authenticating the request; and transmitting the volunteer application information to the organization.

In another aspect, the invention provides computer-implemented method for coordinating a response of volunteers, including specialist volunteers and generalist volunteers, to a public health event. The method includes detecting a public health event, identifying a location of an epicenter and storing the location in a memory, and identifying volunteers and receiving centers within a predetermined distance of the epicenter. Identifying volunteers includes receiving volunteer and location data reflecting a current position of the volunteers or a position to which the volunteers have indicated an ability to report. Identifying receiving center includes comparing receiving stored center locations against the location of the epicenter. Specialist volunteers are assigned to receiving centers within the predetermined distance of the epicenter. Generalist volunteers are assigned to receiving centers within the predetermined distance of the epicenter. Specialist and generalist volunteers are notified of their respective assignments.

BRIEF DESCRIPTION OF THE FIGURES

The foregoing discussion will be understood more readily from the following detailed description when considered with the accompanying drawings, wherein.

The present invention will now be described in more detail with reference to exemplary embodiments thereof as shown in these accompanying drawings. While the description below makes reference to exemplary embodiments, it should be understood that the present invention is not limited thereto. Those of ordinary skill in the art having access to the teachings herein will recognize additional implementations, modifications, and embodiments, as well as other fields of use, which are within the scope of the present invention as described herein, and with respect to which the present invention may be of significant utility.

DETAILED DESCRIPTION

Various disclosed embodiments facilitate communication and coordination among a variety of entities concerned with providing volunteer healthcare funding, equipment and services. Generally speaking, the system allows participation of five categories of users: 1) organizations; 2) patients; 3) volunteers; 4) case workers; and 5) donors. Organizations such as Non-Governmental Organizations (NGOs), hospitals and non-profits facilitate the provision of volunteer healthcare services by leveraging their existing physical infrastructure or relationships to arrange, sponsor or operate health-related projects in need of volunteers worldwide. Users include patients in need of free or substantially reduced-cost health services, such as the uninsured, underinsured, or homeless. Volunteers include various healthcare and medical professionals, nurses, technicians and students that volunteer their time, effort and skills to those in need. Volunteers can also indicate that they are "trainable volunteers," volunteers with an interest in health care volunteering who may have limited knowledge of health care or none at all. A trainable volunteer may have no professional training in a specific health care function. Case workers are special types of volunteers who can be provided with an alternative login and be anyone, ranging from a parent trying to assist their minor child or a certified social worker (e.g. holders of a masters or bachelors degree in social work). Case workers have the ability to register and act as the contact point for patients who do not have a reliable address, telephone number, email address or other contact information. Donors may include a variety of organizations such as corporations, hospitals, NGOs, non-profits and wealthy individuals that are willing to provide financial assistance, equipment or supplies, or even people. With the exception of the patients; each of the users may function alternately as a recipient of healthcare-related services/materials or as a provider thereof.

Figure 1:
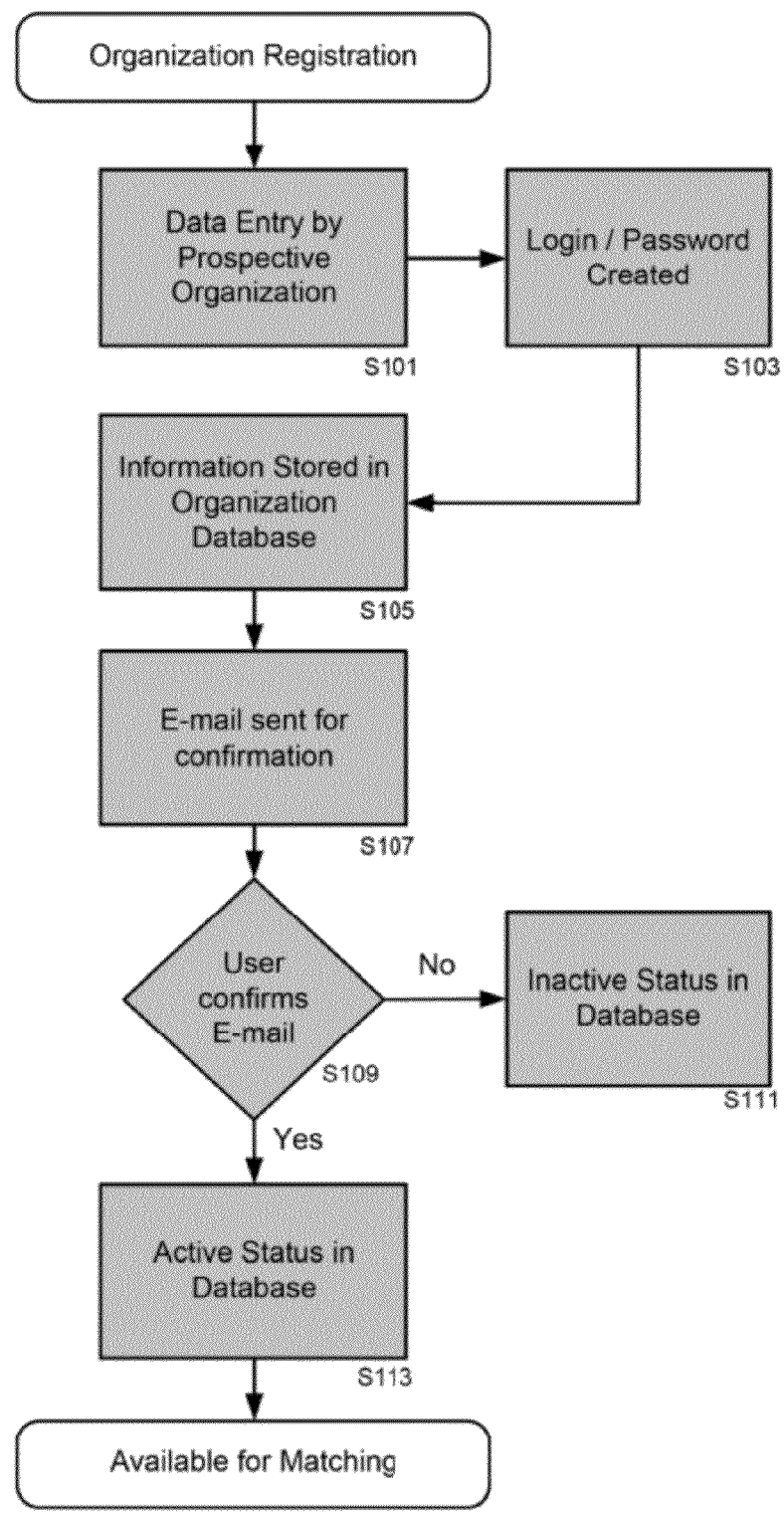
FIG. 1 illustrates an exemplary flowchart for an organization registration process.

FIG. 1 illustrates an exemplary flowchart for an organization registration process. Upon logging into the system, a prospective organization enters (S101) identifying information to create a profile. Identifying information for the prospective organization includes, for example, the organization's name, contact information, and organization type (e.g. NGO, non-profit, hospital, corporation). Login information, such as a username and password, is created (S103). The login information and profile are stored (S105) in a database. A confirmation email is sent (S107) to an address as specified in the organization profile. In one embodiment, the email includes a link that the user may use (S109) to confirm receipt. If a predetermined time elapses after the confirmation email is sent without a response, the organization profile is flagged (S111) as inactive or deleted from the stored list of pending organization accounts in the database. If receipt of the email is confirmed, the organization profile is marked (S113) as active, and the organization can become an active participant in the healthcare volunteer network.

In one embodiment, the organization can designate one or more managers or points of contact. The organization may also input contact information for each of these managers. To create a project or opportunity, the organization can either provide a link to its own project database containing data describing the project, or it can create a project listing stored on the system. The project listing can include a designated project manager or contact, a description of the project, requirements for volunteers and requested donations of equipment, supplies, medicines, volunteers (human resources) or monetary funds. The system allows organizations to create and manage multiple projects or opportunities, each with its own respective point of contact, application process, team of volunteers, supply lists, donation sources, etc. Organizations and donors can also securely link their equipment/supply inventory databases to the system or store and manage their inventory on the system.

Figure 2:
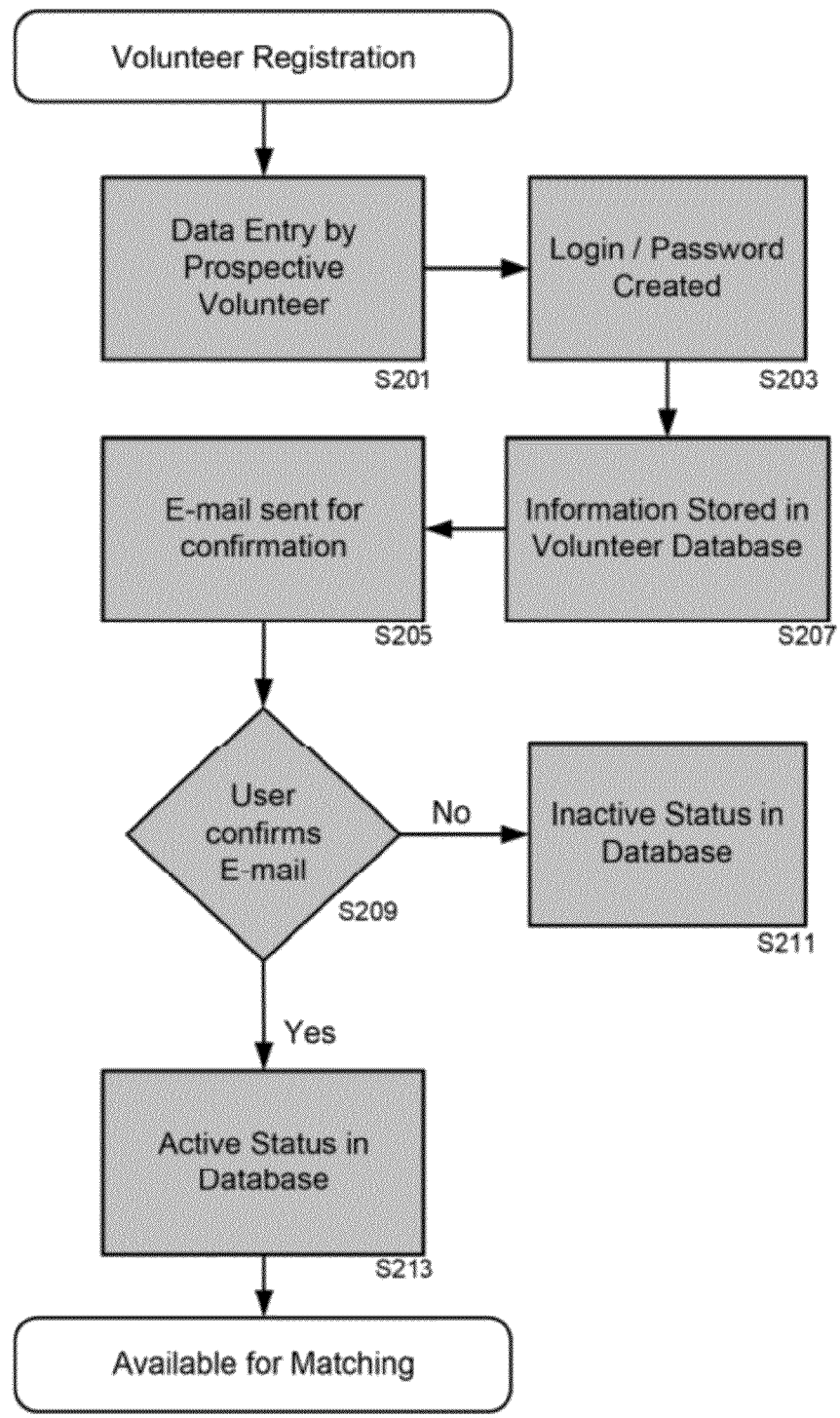
FIG. 2 illustrates an exemplary flowchart for a volunteer registration process.

FIG. 2 illustrates an exemplary flowchart for a volunteer registration process. Similar to the organization registration process, a healthcare volunteer enters identifying information to create (S201) a profile. Identifying information for the prospective volunteer includes, for example, name, contact information, title, education, and professional experience. As other forms of identification, a volunteer may also input one or more of a mobile phone number, a network device address (e.g. MAC, IMSI), or social network or service addresses (e.g. Twitter, LinkedIn, Facebook). By providing one or more points of contact, a volunteer can receive mobile alerts directly on a mobile device. In addition to handset or GPS-type location, other methods such as WiFi and IP location are also suitable to generate location estimates used by the system. In another embodiment, the system links the volunteer's healthcare volunteer account with other of the volunteer's accounts for synchronization or other uses (e.g. importing contacts, inviting friends, viewing current contacts that are also on the healthcare volunteer network).

Login information, such as a username and password, is created (S203). The login information and volunteer profile are stored (S205) in a database. A confirmation email is sent (S207) to an address as specified in the volunteer profile. In one embodiment, the email includes a link that the user may use (S209) to confirm receipt. If a predetermined time elapses after the confirmation email is sent without a response, the volunteer profile is flagged (S211) as inactive or deleted from the stored list of pending volunteer accounts in the database.

If receipt of the email is confirmed, the volunteer profile is marked (S213) as active, and the volunteer can actively participate in the healthcare volunteer network.

In one embodiment, the volunteer is initially presented with a partially-completed common application including basic identification information and information that is generally relevant to the rest of the healthcare volunteer community. This enables organizations to search for potential volunteers for their opportunities and projects based on specified criteria. For example, the common application may allow the volunteer to input information relating to the volunteer's background or interests, such as the volunteer's religion (e.g. Buddhist, Catholic, Christian, Hindu, Jehovah's Witness, Jewish, Mormon, Muslim, and Baha'i), academic discipline (e.g. Medicine, Premed, Dental, Predental, Nursing, Pharmacy, Prepharmacy, Veterinary, Preveterinary, Optometry, Preoptometry, Public Health Policy Students, Business, Law), and/or work function (e.g. Trainable Volunteers, Allergy, Immunology, Anesthesiology, Cardiology, Carpenter, Certified Nursing Assistant, Chinese Medicine, Chiropractor, Colon and Rectal Surgery, Critical Care Medicine, Cytotechnologists, Dental Assistant, Dental Hygiene, Dental Hygienist, Dentistry, Dermatology, Dietitian, Driver, Emergency Medicine, EMT Basic, EMT/Paramedic, Endocrinology, Endodontics, Engineer, Family Medicine, Gastroenterology, General Preventive Medicine, Geriatric Medicine, Health Educator, Hematology and Oncology, Infectious Disease, Internal Medicine, Kinesiology, Licensed Professional Counselor, Licensed Practical Nurse, Massage Therapist, Medical Assistant, Medical Billing and Coding, Medical Lab Technologists, Midwifery, Master of Public Health, Nephrology, Neurological Surgery, Neurology, Nuclear Medicine, Nurse, Nurse Practitioner, Obstetrics and Gynecology, Occupational Medicine, Ophthalmology, Optometry, Optometry Student, Oral and Maxillofacial Pathology, Oral and Maxillofacial Radiology, Oral and Maxillofacial Surgery, Orthodontics, Orthopaedic Surgery, Otolaryngology, Pathology, Pediatric Cardiology, Pediatric Dentistry, Pediatrics, Periodontics, Pharmacy, Phlbotomist, Photographer, Physical Therapy, Physician Assistant, Plastic and Reconstructive Surgery, Podiatry, Prosthodontics, Psychiatry, Public Administration, Public Health, Pulmonary, Radiation Therapy, Radiology, Rheumatology, Sonographer, Student, Surgery-General, Surgical Technology, Thoracic Surgery, Trauma Surgery, Urology, Vascular Surgery, Veterinary), non-health profession, language skills, willingness to travel, etc.

In another embodiment, an organization may create a custom application associated with the organization including, e.g., additional questions or criteria that are not included on the common application. The custom application may further include a diagnostic for testing a volunteer's leadership, personality traits or teamwork preferences and aptitude. Alternatively or in addition, an organization may create custom applications corresponding to its volunteer opportunities or projects.

Figure 3:
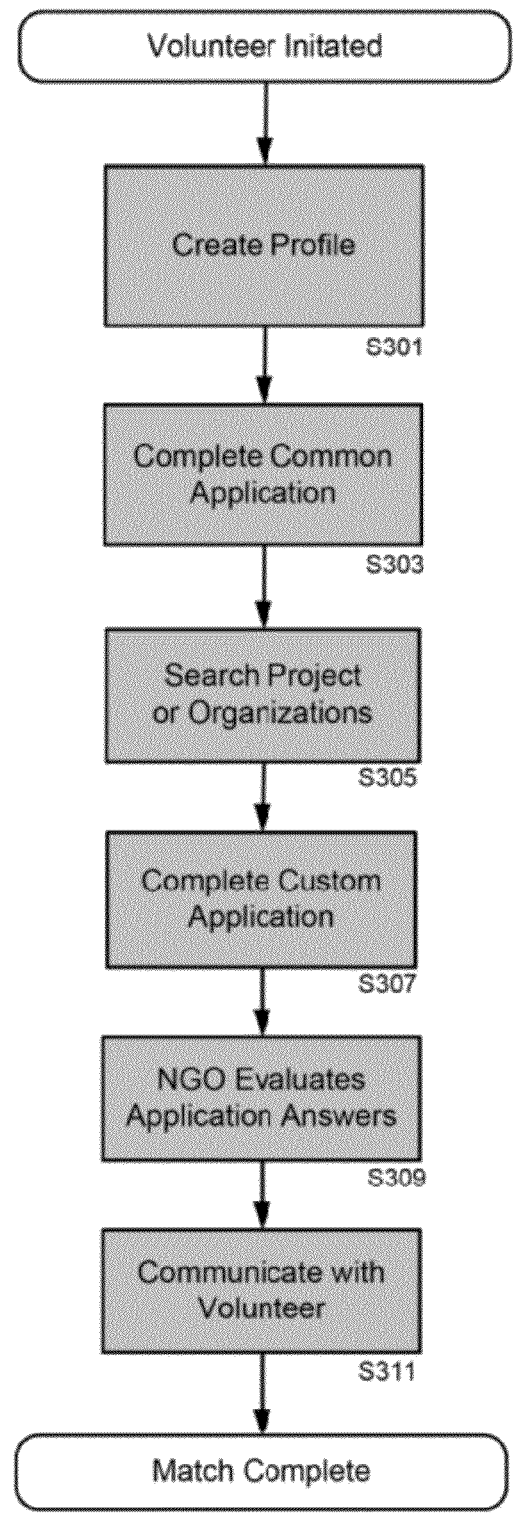
FIG. 3 illustrates an exemplary flowchart for a volunteer-initiated application process including common and custom applications.

FIG. 3 illustrates an exemplary flowchart for a volunteer-initiated application process including common and custom applications. After registering with the system and creating (S301) a profile, the volunteer is prompted to complete (S303) a common application. Once the common application is complete, the volunteer can search (S305) for projects or organizations using keywords or search criteria. Based on the search criteria, the volunteer can browse the search results and review information input by the sponsoring organization describing the opportunity. The system may optionally allow users to search for opportunities without completing the common application, but then require the common application to be completed before the user applies to any particular organization or project.

After the volunteer selects one or more opportunities, the volunteer is prompted to complete (S307) a custom application designed by the organization including questions more tailored to the organization and/or project than those included in the common application. For example, the common application may ask the volunteer to indicate a willingness to travel internationally, while a customized application for Médecins Sans Frontières (Doctors Without Borders) may ask whether the volunteer is willing and authorized to travel to Haiti to treat earthquake victims. Either or both of the common and custom applications can include diagnostics such as psychometric questionnaires like the Myers Briggs personality test. In other embodiments, the customized application can also include diagnostics relating to the particular project or the project role for which the volunteer is applying. For example, if the volunteer is applying to be a manager, the custom application may include a leadership test. If the volunteer is applying for a support position, the custom application may including a test for teamwork skills and styles.

The volunteer's inputs to the common application and/or the custom application are then scored or evaluated (S309) against the criteria desired by the organization. In one embodiment, the organization can electronically review the volunteer's responses to the common application and the custom application. Alternatively, the volunteer's responses can be automatically evaluated against criteria set by the organization, and then only applicants meeting a predetermined threshold score are presented to the organization for full consideration. The organization can then choose to communicate with one or more volunteers (S311) via email, a message sent using the system's internal messaging subsystem, text message, phone, video, VoIP or other digital messaging system.

Figure 4:
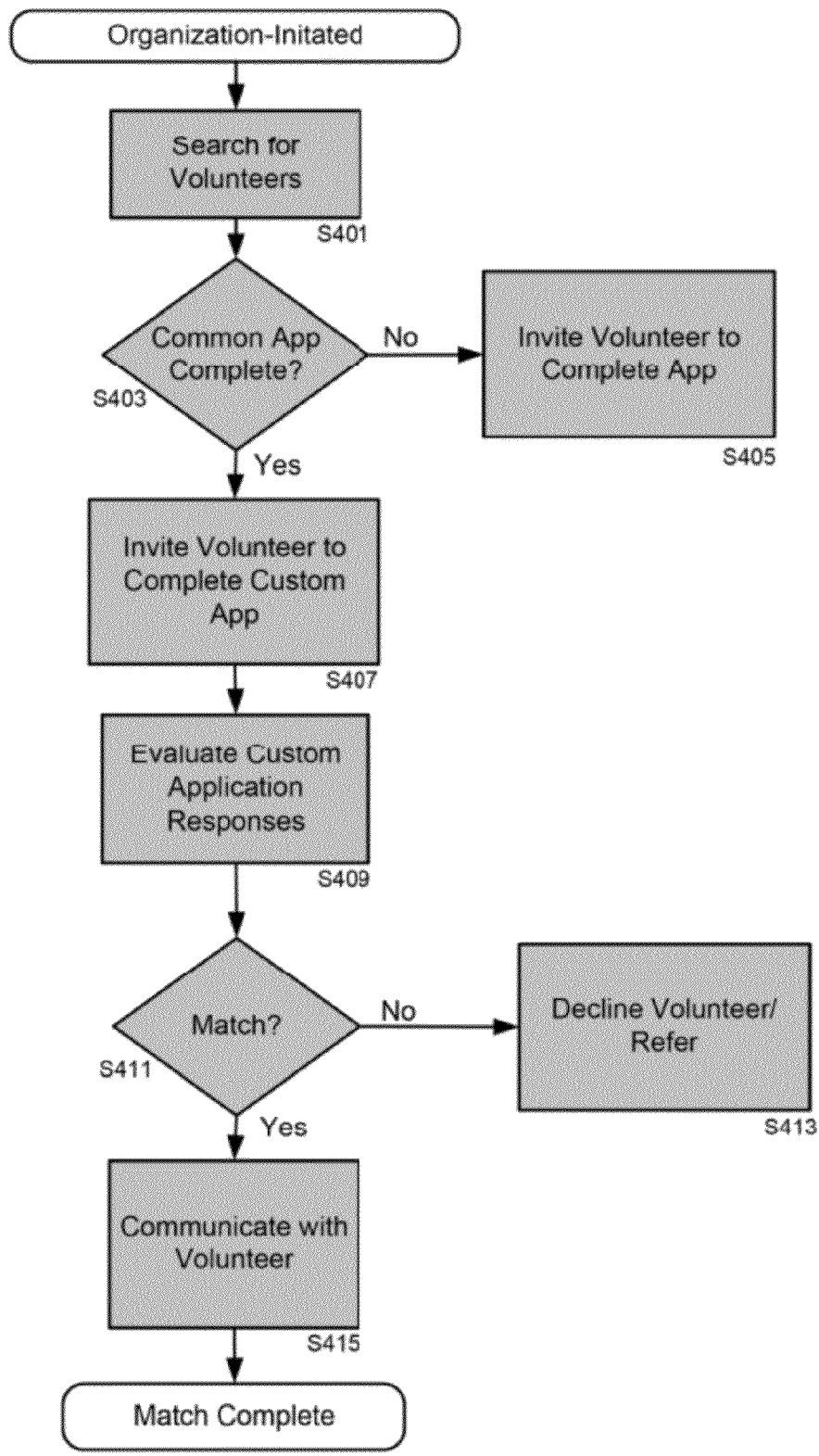
FIG. 4 illustrates an exemplary flowchart for an organization-initiated application process including common and custom applications.

FIG. 4 illustrates an exemplary flowchart for an organization-initiated application process including common and custom applications. Using the system, organizations can search (S401) for volunteers based on keywords or search criteria. In one embodiment, this search parameters are input by an organization worker performing a query of the volunteer database. In another embodiment, the system performs the search automatically at predetermined intervals to keep the organization up-to-date on new volunteers and newly updated volunteer profiles. Further, the search can also be performed upon the posting of a new project or opportunity, where the organization creates a volunteer search corresponding to that particular project.

Based on the search, a list of potential volunteers is returned (S403) for those volunteers with complete common applications. If the potential volunteer hasn't completed the common application, then the organization can choose to overlook the volunteer or invite (S405) the volunteer to complete his or her common application. If the volunteer has already completed the common application, the organization can invite (S407) the volunteer to complete a custom application corresponding to the organization generally or to a particular project. Upon receiving the completed custom application, the volunteer's responses are evaluated (S409) and the system determines (S411), according to criteria predetermined by the organization, if the volunteer is a match. If an application doesn't meet the organization's criteria, the organization can decline (S413) the volunteer's application. The organization can also refer the volunteer to apply to another project or organization that may be a better match. If the volunteer is a match, the organization can communicate (S415) with the volunteer using email or a messaging service.

In one embodiment, the system provides for a project-driven automated search for volunteers or donations. For example, an organization creates a new opportunity or project entry on the system and inputs parameters for desired volunteers including, for example, the respective skills, background and interests of the desired volunteers. The system then searches the volunteer database and recommends volunteers to the organization. A similar automated search can be done to identify needed supplies, equipment or funding from donors. In one embodiment, the search occurs automatically at predetermined intervals and for a predetermined duration (for example, for as long as there are open positions for the opportunity/project or until the project is cancelled). The organization is presented with a list of recommended volunteers that it can rank or sort by any of the search parameters. Using this list, the organization selects one or more volunteers to message or "invite" to complete a custom application. In another embodiment, the organization is presented with a list of needed supplies that have been requested but are unavailable on one or more of the donation inventory lists linked to or stored on the system.

In one embodiment, the system securely accepts and stores documents, such as copies of passports, diplomas, proofs of malpractice insurance, letters of recommendation or reference, certificates and medical licenses. The volunteer may upload one or more of these documents in connection with the common application and/or in connection with an organization's or project's custom application. Alternatively, the volunteer may upload these documents after being matched with an organization or project. Securely uploading and storing copies of these documents allows volunteers and organizations to share documents relating to project staffing, especially for international projects. For example, the volunteer may open a secure network connection with the system, and upload one or more documents for storage on the system. These documents would then be stored securely in a system database and accessible only to the volunteer unless and until the volunteer chooses to share access to the documents with one or more selected organizations. In another embodiment, the volunteer uploads a digital certificate corresponding to a paper document. In one embodiment, the system authenticates one or more of the volunteer's credentials electronically. For example, the volunteer can be is prompted to enter an identifier such as a username or registration number, along with appropriate password or pin information, to allow the system to automatically and independently verify the volunteer's credentials against, for example, an electronic database of registered medical practitioners. Additionally, the system can use the volunteer's information, such as name, address, social security number, or license number, to check the volunteer against a variety of law enforcement and professional discipline lists to alert organizations of potential issues with the volunteer.

Figure 5A:
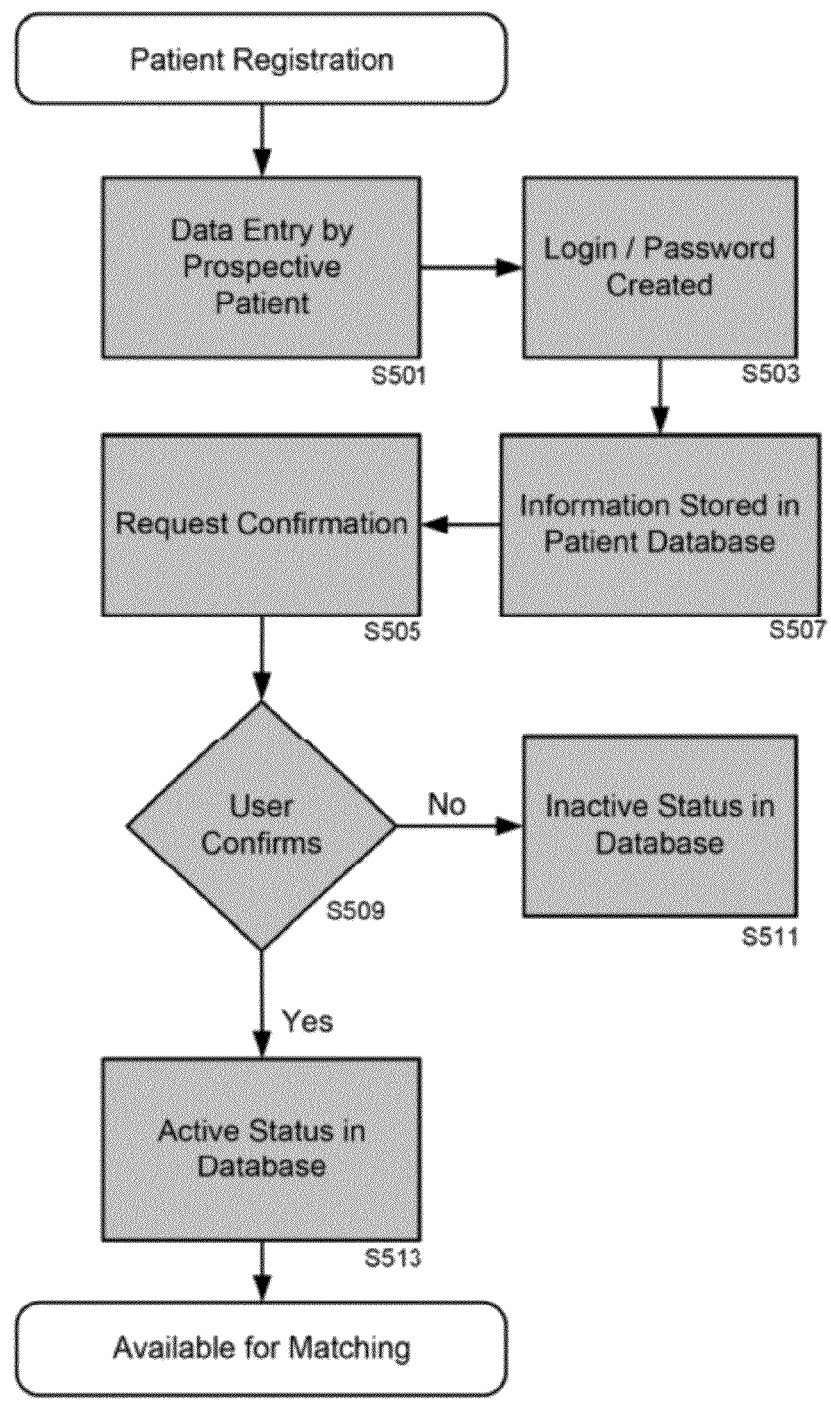
FIG. 5A illustrates an exemplary flowchart for a patient registration process.

FIG. 5A illustrates an exemplary flowchart for a patient registration process. A patient or a caseworker enters (S501) identifying information for the patient to create a profile. Understanding that patients in need of the volunteer services provided through the system often lack Internet access, a caseworker can enter the patient's information. Identifying information for the patient includes, for example, name, contact information, age, gender, previous or concurrent medical providers, requested medical assistance, and an explanation of why free medical care is needed (e.g. a declaration of no or insufficient insurance, lack of funds). Patient information can also include a listing of one or more shelters, food kitchens or clinics where the patient has visited. If the patient has or had contact with a case worker, the contact or identification information of the case worker can be included in the patient profile. Additionally, the profile may include contact or identification information of the patient's next of kin. To assist in verifying the identity of patients, a photo or other description of identifying physical characteristics (e.g. birthmarks, scars) may also be input and stored by the system. Login information, such as a username and password, is created (S503). The login information and patient profile are stored (S507) in a database. A confirmation request is sent to the user (S505), for example, by sending a confirmation email to an address as specified in the patient profile. In one embodiment, the email includes a link that the user may use to confirm (S509) receipt. In another embodiment, the link includes a captcha or other security measure. Other suitable measures for providing secure and accurate confirmation can be used, including without limitation telephone, text, smartcards, security tokens, retina scans and fingerprint analysis. The patient profile is flagged (S511) as inactive or deleted if a predetermined time elapses without a response to the confirmation email. If confirmed, the patient profile is marked (S513) as active, and the patient can seek assistance through the healthcare volunteer network.

Figure 5B:
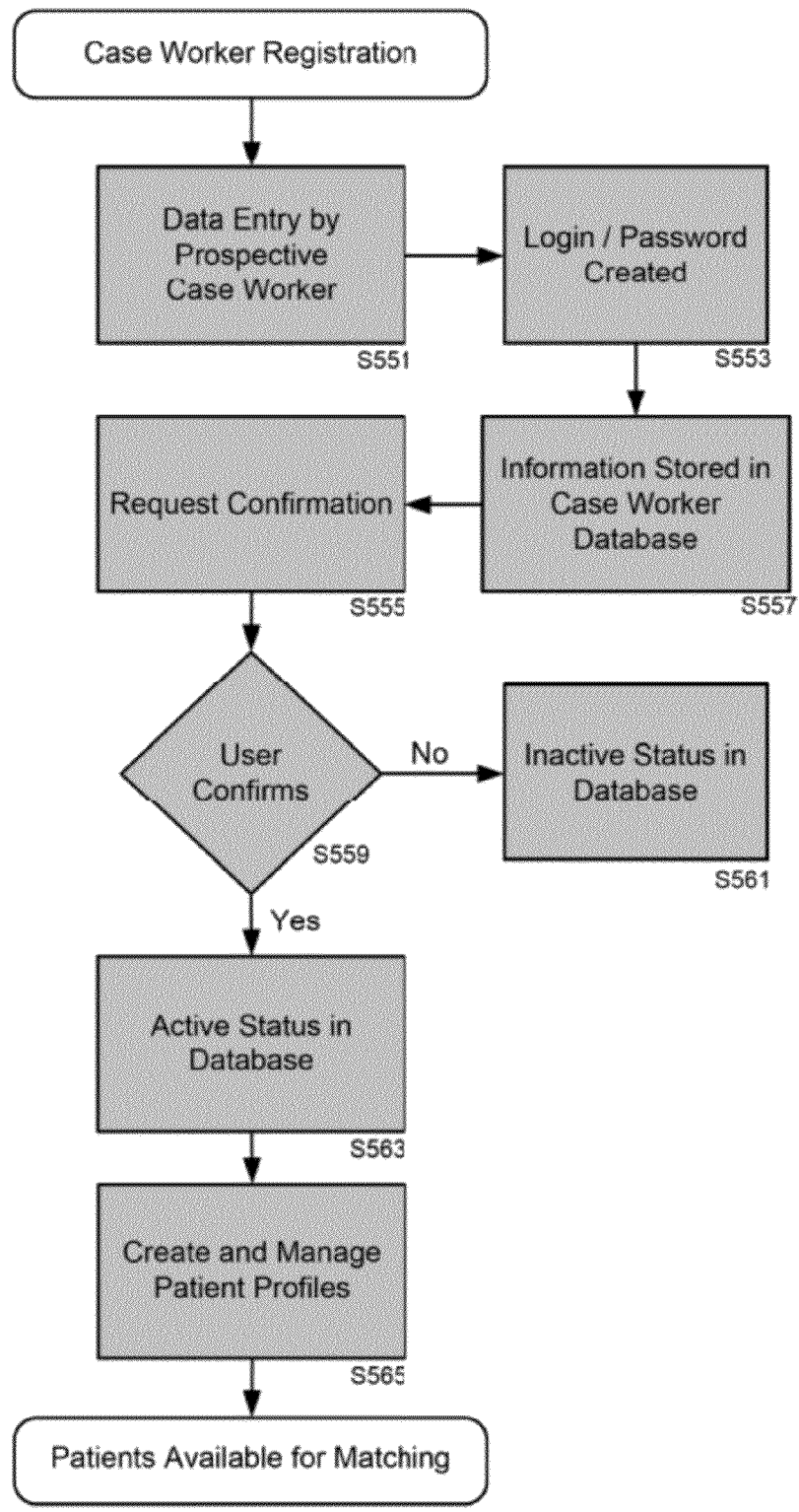
FIG. 5B illustrates an exemplary flowchart for a case worker registration process.

FIG. 5B illustrates an exemplary flowchart for a case worker registration process. Understanding that patients in need of the volunteer services provided through the system often lack Internet access, in one embodiment, a caseworker enters and manages identification and medical information for one or more patients. A case worker creates a profile (S551). Case worker login information, such as a username and password, is created (S553). The login information and case worker profile are stored (S557) in a database. A confirmation request such as a confirmation email is sent (S555) to an address as specified in the case worker profile. In one embodiment, the email includes a link that the user may use to confirm (S559) receipt. In another embodiment, the link includes a captcha or other security measure. Other suitable measures for providing secure and accurate confirmation can be used, including without limitation telephone, text, smartcards, security tokens, retina scans and fingerprint analysis. The case worker profile is flagged (S561) as inactive or deleted if a predetermined time elapses without a response to the confirmation email. If confirmed, the case worker profile is marked (S563) as active, and the case worker can help patients obtain healthcare through the volunteer network. Once the case worker has an active profile, the caseworker then creates one or more patient profiles (S565) with patient information as described above. If the patient has or had contact with another case worker or clinic, the contact or identification information of the other case workers or clinics can be included in the patient profile. To assist in verifying the identity of patients, the case worker may upload a photo or other description of identifying physical characteristics to be stored by the system. The case worker can also input other notes relating to the case worker's interactions and impressions of the patient.

Figure 6:
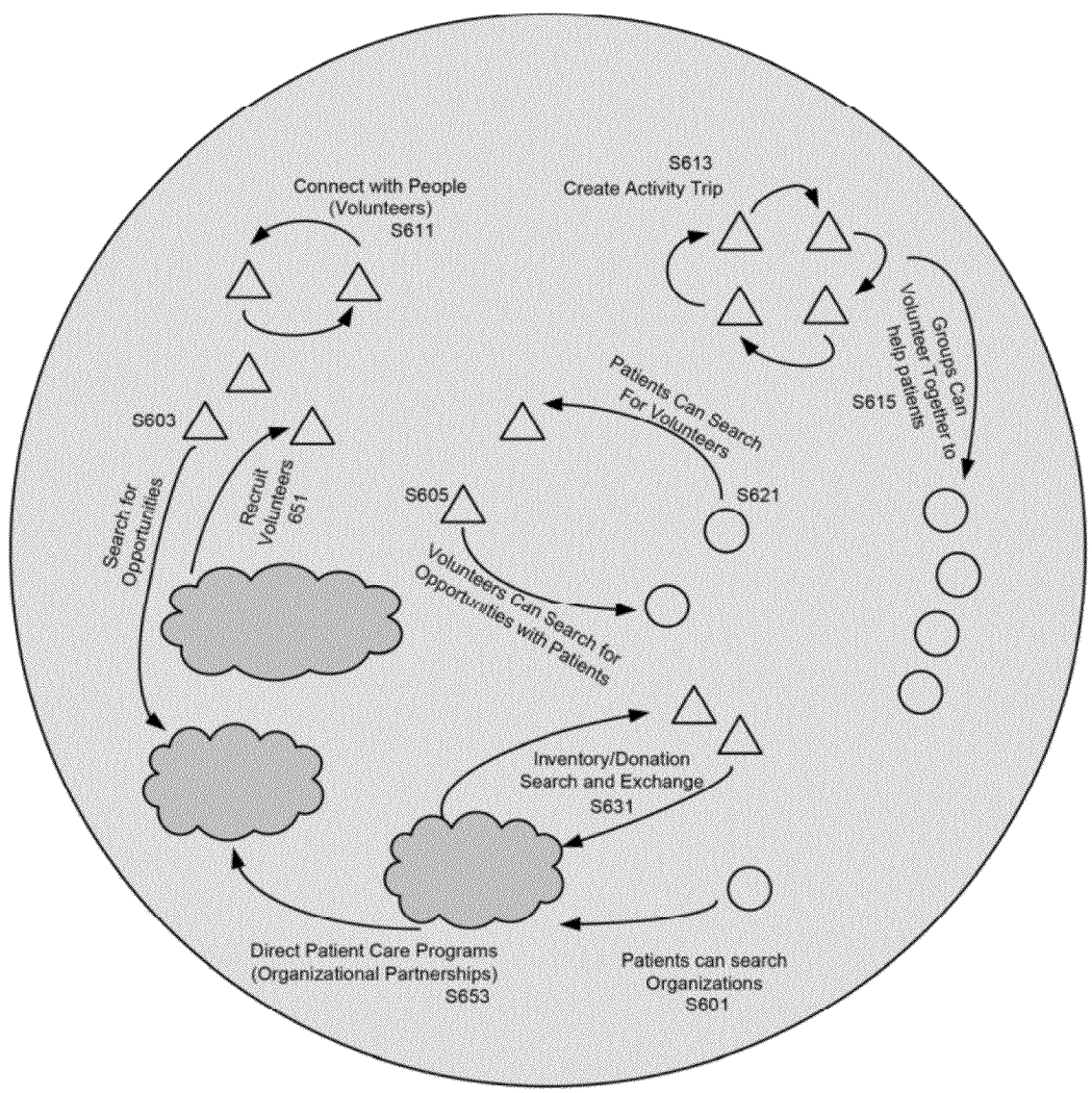
FIG. 6 is a schematic diagram illustrating exemplary networking functions and possibilities.

FIG. 6 is a schematic diagram illustrating exemplary social networking capabilities facilitated by disclosed embodiments. For example, patients (represented by circles) can search (S601) for organizations offering healthcare services. Volunteer users (represented by triangles) can search (S603) for volunteering opportunities with particular organizations using keywords or search criteria, as well as (S605) for patients in need of healthcare services. Further, using the system, volunteers can connect (S611) with other volunteers or partner with other volunteers to create (S613) "ad hoc" organizations and projects to help (S615) patients in need. One or more volunteers can also propose projects and activities to a particular organization for sponsorship or seek donations and other volunteers to accomplish the project on their own. Volunteers can also create a group to volunteer for an organization's project. Patients, either themselves or through a case worker, can search (S621) for volunteers. Organizations can recruit (S651) volunteers and partner (S653) with other organizations in direct patient care programs. Moreover, organizations and volunteers can search for donors (financial, equipment, supplies, logistical services), and donors can search for organizations, volunteers and patients satisfying their donation criteria (S631).

Figure 7:
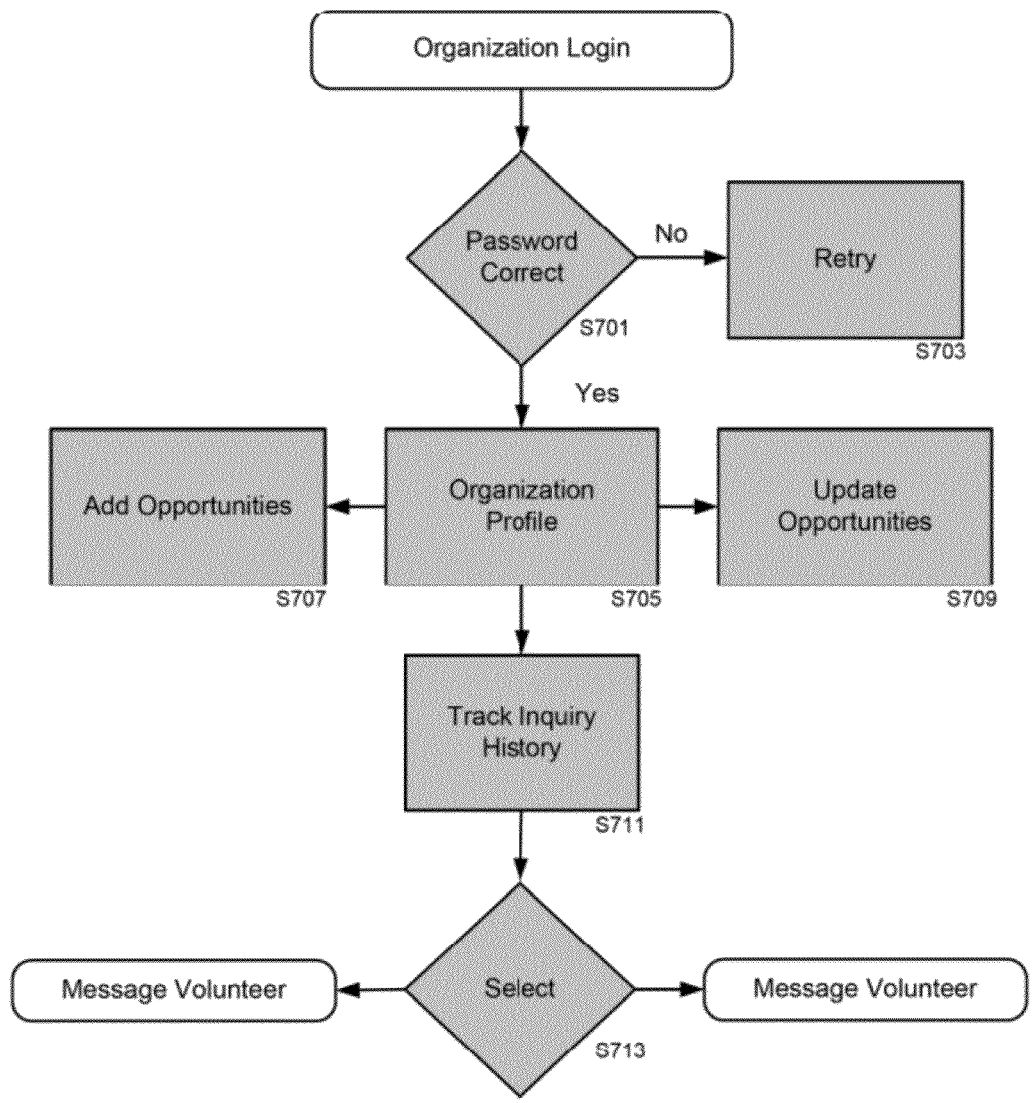
FIG. 7 illustrates an exemplary flowchart for an organization matchmaking process.

The system allows an organization to effectively manage their various projects and volunteers. FIG. 7 illustrates an exemplary flowchart for an organization matching process, through which an organization searches for volunteers matching keywords or meeting criteria corresponding to the organization's needs and the needs of particular projects. Upon logging (S701) into the system, the organization can manage (S705) its profile and add (S707) or update (S709) posted volunteer opportunities. Additionally, the organization can track (S711) inquiries from volunteers regarding its posted opportunities or inquiries sent to the organization generally. These inquiries may also take the form of project proposals, where a volunteer or other user proposes that the organization engage or involve itself in a new or existing project not currently listed by the organization. The organization can also search for volunteers using keywords or search criteria. For example, search criteria may include seeking a vascular surgeon with over 5 years post-fellowship experience with a willingness to travel into dangerous situations.

Additionally or in the alternative, the organization is presented with recommendations for volunteers based a comparison of criteria input by the organization corresponding to a particular project/opportunity and the information input by volunteers. Searching can optionally include using a mapping system (GIS) to find volunteers within a certain area. In one embodiment, the recommendations are based on volunteers that match the organization's criteria for an opportunity or project. Additionally or in the alternative, the recommendation includes volunteers matching related or complementary criteria to a selected volunteer or another recommended volunteer. For example, if an organization requires an orthopedic surgeon for a particular project, in addition to one or more matching surgeons, the system may recommend nurses or technicians with related surgical support experience. Based on the search results and/or recommendations, the organization is able to then select (S713) volunteers to contact, for example, via email. In one embodiment, messaging among various system entities is done using a messaging protocol with mailboxes that do not require email accounts in domains external to the system. Alternatively, the system interfaces with other, external systems to communicate with volunteers by text message (SMS), IP-based instant message, or social network messaging protocols such as Facebook and LinkedIn.

The system further assists organizations with the management of their volunteers. For example, as volunteers are accepted for one or more projects, the system tracks which volunteers are associated with the various organizations and projects. The organization can generate staffing reports of its volunteers using the system, and also view the availability of current and prospective volunteers to maintain staffing levels for its projects.

Various embodiments provide users with integrated inventory management functionality to facilitate the efficient procurement of needed equipment and supplies. Organizations may have inventory of their own to manage and donate, or the organization may need to obtain money, equipment or supplies for their own projects. In one embodiment, volunteers and organizations can input requests into the system for certain equipment or supplies, which are saved in the database as requested items. Donors can then search for or scroll through a list of requested items. The system database includes product, manufacturer and corporate contact information for donation requests. In one embodiment, the system compares the donor's uploaded or updated inventory list against the list of requested items to identify one or more items as potential donation matches. The requesting party (e.g. organization, volunteer) or the donor (or both) are notified of the potential donation match. Generally, organizations and donors can input their available inventory data into the system directly, or maintain a link between the system and the organization/donor's own inventory system to provide users of the system with views of real-time inventory availability. In the inventory database, information for each item is provided. The description can include, without limitation, an item description (e.g., sigmoidoscope), condition (e.g., new, sealed, used, uncontaminated, contaminated, sterile, nonsterile), brand, model, manufacture year/age, serial number, medical specialty (e.g., dentistry, cardiology, general surgery), purchase price, market price, tax treatment, hyperlink to product web site, product photo, weight, location(s) or address(es) at which the item is being held, dimensions, and quantity. Further, each posted item or group of items also includes a status indicator. For example, the indicator may reflect that the item is immediately available, available on future date, available until future date, backordered, unavailable, reserved, or pending/requested. The indicator may be set to pending if, for example, there is an outstanding inquiry about that item from another user.

Figure 8A:
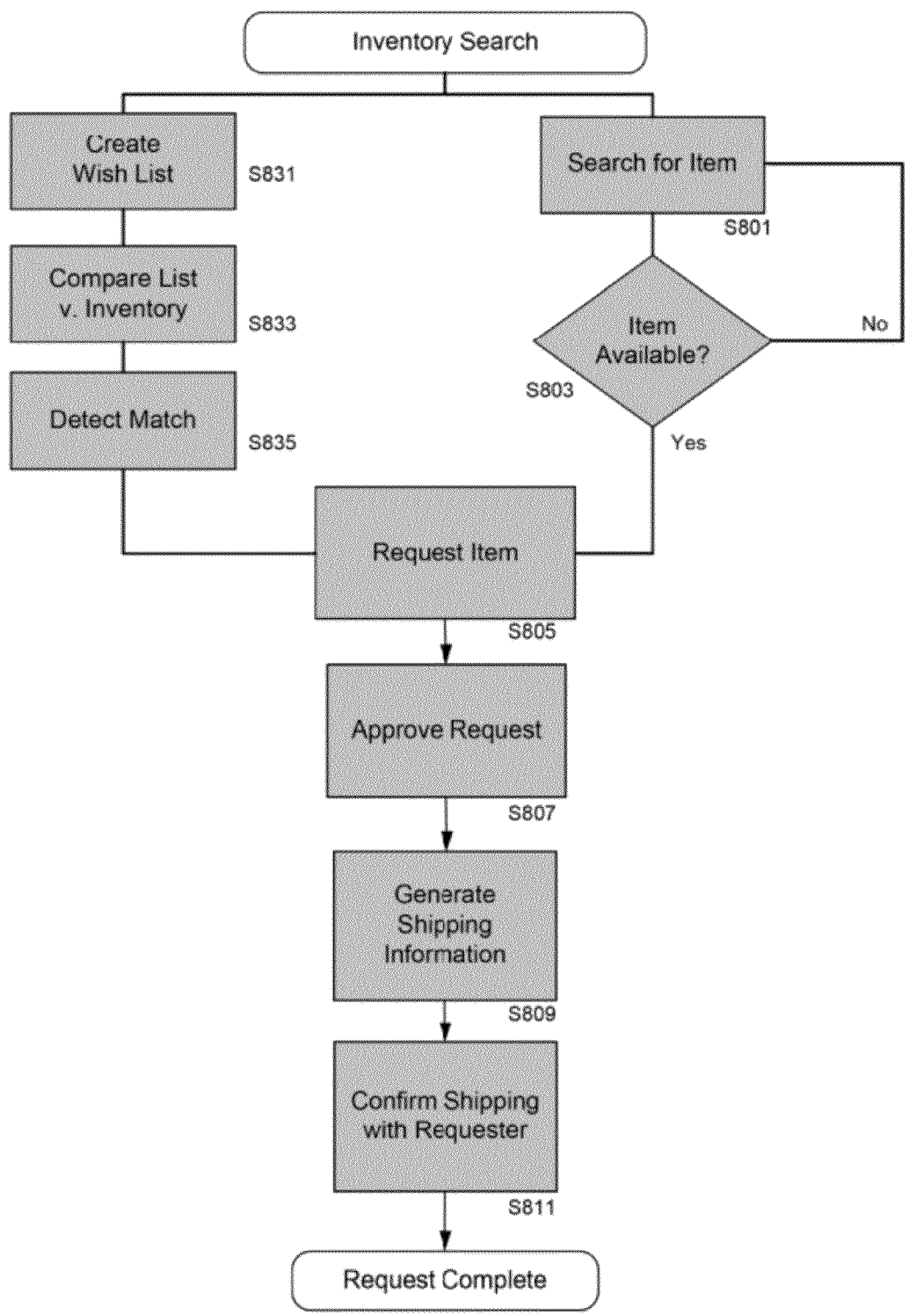
FIG. 8A illustrates an exemplary flowchart for an inventory search process.

FIG. 8A illustrates an exemplary flowchart for an inventory search process. Through the system, volunteers and organizations can search (S801) one or more inventory lists to request equipment and supplies. In one embodiment, the system employs an interface similar to an online shopping cart, whereby available items can be browsed, added or removed to a virtual cart. The search can utilize any combination or keywords or search criteria, including the item's condition, shipment method (e.g. donor pays shipping fees, organization pays shipping fees, pick-up in person, or multiple possibilities), location, and availability. In addition to a description of the item, the system shows the item's availability (S803). If the item is available, the user can request (S805) the item, causing a message to be sent to the donor or provider of the requested item. If the item is not available, the user can request the item from a donor (whereby a message is sent to the donor's account) or have the item request added to the requested item list, viewable by individual and corporate/organizational donors. The donor can then choose to approve (S807) the request. In one embodiment, the request for the item includes an explanation by the requester describing the intended use of the equipment or supplies. In another embodiment, the donor is provided with a link to a profile of the particular organization, project or activity (including an ad-hoc organization/activity formed by a group of volunteers) for which the item is being requested. If the donor agrees with the use, the donor can approve (S807) the request. At that point, the status of the item or items is changed to reflect that the item is no longer available to other users (e.g. pending, unavailable). In one embodiment, the system then generates (S809) shipping information including, for example, an invoice number and a packing slip. Upon shipment of the order, the system may transmit a message to the requesting organization or volunteer confirming (S811) shipment. In one embodiment, the system permits the recipient to indicate that the recipient will pick up the shipment in person, pay on delivery, etc. Embodiments of the system allow for shipment initiation and tracking by integrating package and shipping status information through interfaces with commercial software platforms such as FedEx's PIS Ship, UPS's Quantum View, the US Postal Service, DHL and other available shipping methods. The data from these systems can be imported and associated with the listed items so both recipients and donors can effectively initiate and track shipments of donated supplies and equipment.

In another embodiment, organizations and volunteers can also create "wish lists" of equipment and supplies (S831). The system then compares the wish list entries with the available inventory listed on the system (S833) and alerts the list owner when an item becomes available (S835). In one embodiment, the project parameters can be used to generate a default or suggested list of supplies and equipment from among the current list of available items. For example, if the project parameters include pediatric care for up to 200 children, some of the suggested items might include 20 thermometers, 2 jars and 10 gallons of nontoxic disinfectant solution. In one embodiment, the suggested list is applied as a search across all available donor inventory to generate requests for these supplies. In the case where one set of requested donations includes items from multiple donors, the system generates a corresponding number of shipping orders.

Embodiments of the system also accommodate and coordinate logistical donations. For example, one embodiment allows whole or partial shipments of donated supplies or equipment to be packaged and shipped for free using automated shipping logistics and services available from FedEx, UPS, etc. Donating shippers can input criteria (dimensions, weight, organization, project, destination, pickup, urgency) into the system to limit the types of donations that it will assist in shipping at no or reduced cost. Further, organizations and volunteers searching for donations can use free shipping as a search criteria. In another embodiment, airlines and travel services list free or discounted airfare as donations. For example, an airline or travel service can designate one or more donated fares for an opportunity/project based on the project's organization, location, volunteer location, etc. Donations such as flights that do not require shipping (or other delivery logistics for physical items) can be listed as available inventory on the system, but be specially coded to distinguish these donations from physical items. The special fares can be associated with a particular project or be made available generally to volunteers involved with projects meeting one or more of the donor's predetermined donation criteria. To access the special fare, a volunteer who commits to a project may be provided with authorization to link directly to an online reservation system to arrange for the donated travel using a special link, certificate or code.

The system further facilitates the matching of financial donors and organizations and volunteers in need. Donors can deposit cash, credit card payments and checks mailed to a central authority providing access to or use of the system. The system allows donors to indicate whether funds are transferred to recipients before a trip/project, after a trip/project or during a trip/project, thereby giving the donor discretion on the timing of the donations and whether particular project milestones or events must be achieved. Donors can search for volunteers, organizations and projects based on keyword or search criteria. For example, donors can search for projects relating to toxic waste poisoning sponsored by an international aid organization with existing funds of under $1 million. Embodiments of the system support wire transfers and other electronic payment forms such as credit card and PayPal®.

Figure 8B:
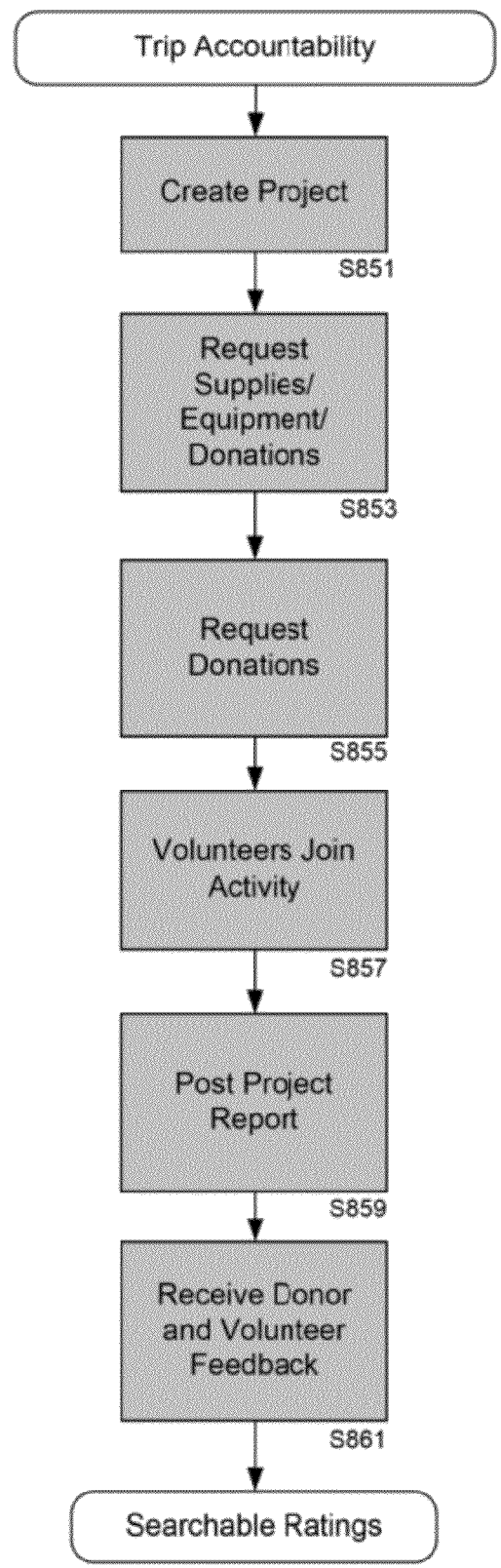
FIG. 8B illustrates an exemplary donation accountability process.

FIG. 8B illustrates an exemplary donation accountability process. As described elsewhere, volunteers and organizations can create volunteer projects, events or activities (S851). In addition to providing a description of the activity, a request for certain services, supplies or equipment can be made (S853). Further, a request for donations or other financial support can be made (S855). Additionally, the activity poster can invite other volunteers to join or have make the activity visible to volunteers searching for activities (S857). Upon the initiation or completion of the activity, a trip progress report or summary is posted to the site, including an expense report, and audited (S859). Photos and other descriptive materials may also be attached. Donors, including companies, non-profit organizations, service providers and individual volunteers then input their feedback and ratings on the activity (S861). This feedback is posted and associated with the activity and the accounts of the entities sponsoring or creating the activity, thereby providing for donation accountability and public feedback.

In one embodiment, financial donations are held until the donor receives and approves the report reflecting the expenses incurred by the volunteers performing the activity. For example, Dr. John Doe MD posts an international activity entitled "Surgeries in Tanzania for Christmas," which is also sponsored by Médecins Sans Frontières. Médecins Sans Frontières might accept Dr. Doe as a sponsored trip. A non-profit organization, individual or other donor then donates funds, using a check, online payment or other method, to be flagged for Dr. Doe's posted activity by transferring it into an escrow account that is tracked and monitored by the system. Once the trip is completed, Dr. Doe, Médecins Sans Frontières or another volunteer posts an electronic report detailing the activities, accomplishments and expenses of the trip. Donors to this activity are notified that the report is available for auditing. Upon approval by the donor(s), the corresponding funds are released to and appropriately apportioned for Dr. Doe, Médecins Sans Frontières and/or another entity associated with the activity posted on the system.

Figure 9:
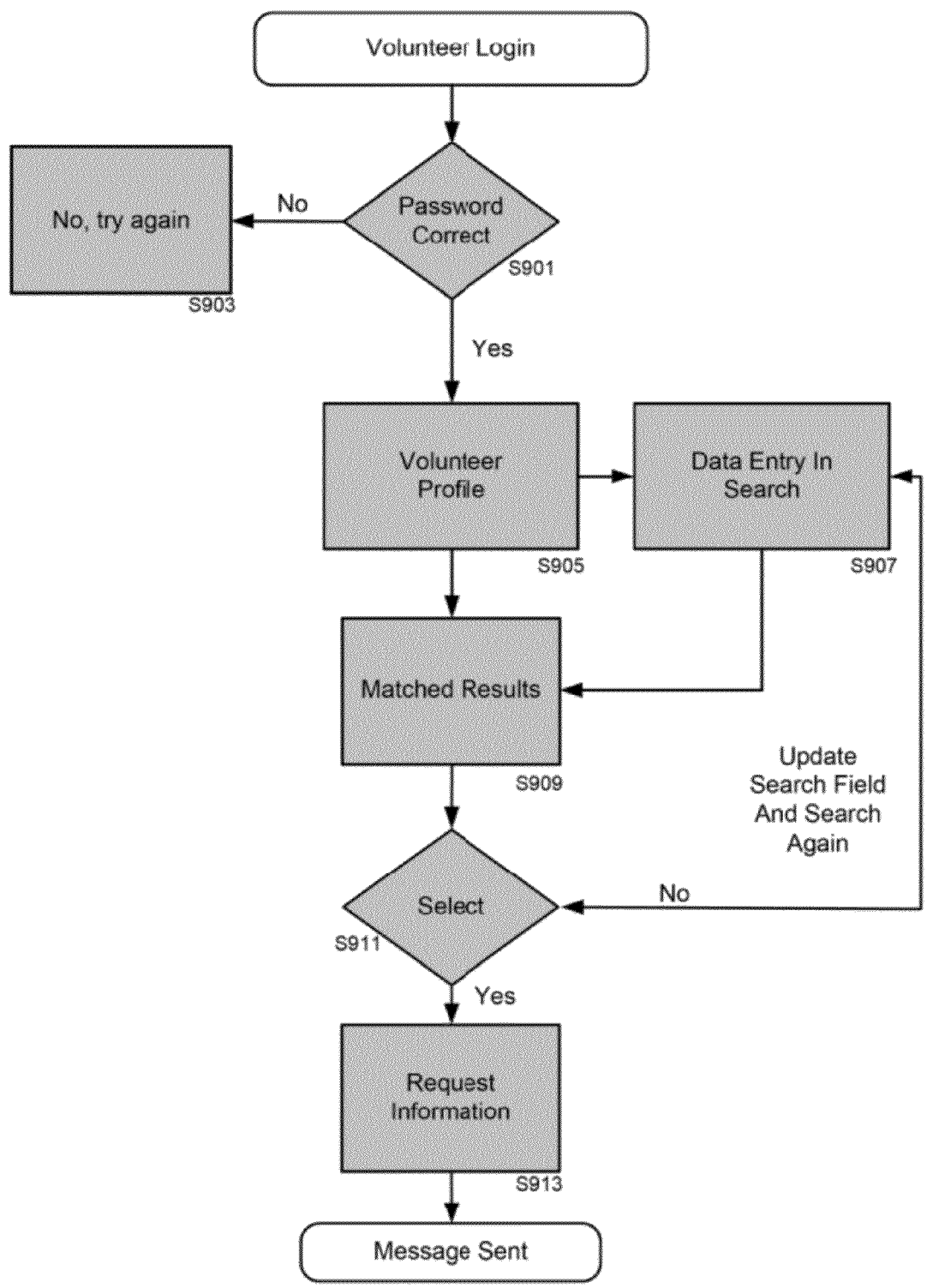
FIG. 9 illustrates an exemplary flowchart for a volunteer matchmaking process.

FIG. 9 illustrates an exemplary flowchart for a volunteer matching process. Once the volunteer logs (S901) onto the system, the volunteer can manage (S905) his or her profile and search (S907) for volunteering opportunities, such as organizations, projects and patients in need. The volunteer enters search criteria to filter out or return matched results. In one embodiment, the search criteria includes location or geographical parameters (e.g. opportunities in Cotê d'Ivoire, opportunities in ZIP 20001, or opportunities within 10 ml of volunteer's home address) and integrates with information services such as the Google Maps API to provide a visual illustration of the search criteria and/or available opportunities. Upon receiving one or more matching results (S909), the volunteer may select (S911) one or more opportunities for applying or for requesting further information from the sponsoring organization (S913).

In one embodiment, volunteers are also able to search for other volunteers. In another embodiment, volunteers can form groups and present themselves to projects and opportunities together. Volunteers can search for other volunteers with similar interests or backgrounds. Additionally, volunteers can search for volunteers with complementary backgrounds in the context of one or more projects. For example, if a volunteer who is a pediatrician is interested in applying for or joining an organization's project relating to care of new mothers in Zimbabwe, the interested pediatrician may initiate a search for other volunteers with backgrounds in reproductive health and invite them to apply to the same project. In another embodiment, the interested pediatrician may use the system to create an electronic invitation to a friend or colleague who is not yet a part of the healthcare volunteer online community.

Volunteers may also indicate their availability to other users on the system. In one embodiment, volunteers commit to providing a certain number of pro bono treatments or hours of service to patients or organizations. Patients and organizations can then search for volunteers based on their remaining pledged treatments or hours of service. Additionally, volunteers may also indicate their availability with respect to time and date, length of time, thereby allowing patients, case workers and organizations to search for them accordingly. By allowing volunteers to indicate their times of availability, this also facilitates organizations seeking to maintain a consistent level of staffing for their projects.

Embodiments of the system also allow for volunteers to track and record their various volunteer activities online, thereby generating a dynamic volunteering "resume" of their volunteer experience or past organizational affiliations. The volunteer can optionally allow this resume to be searchable by patients and organizations. Further, patients and organizations can include types and amount of volunteer experience as search criteria when seeking volunteers.

Figure 10:
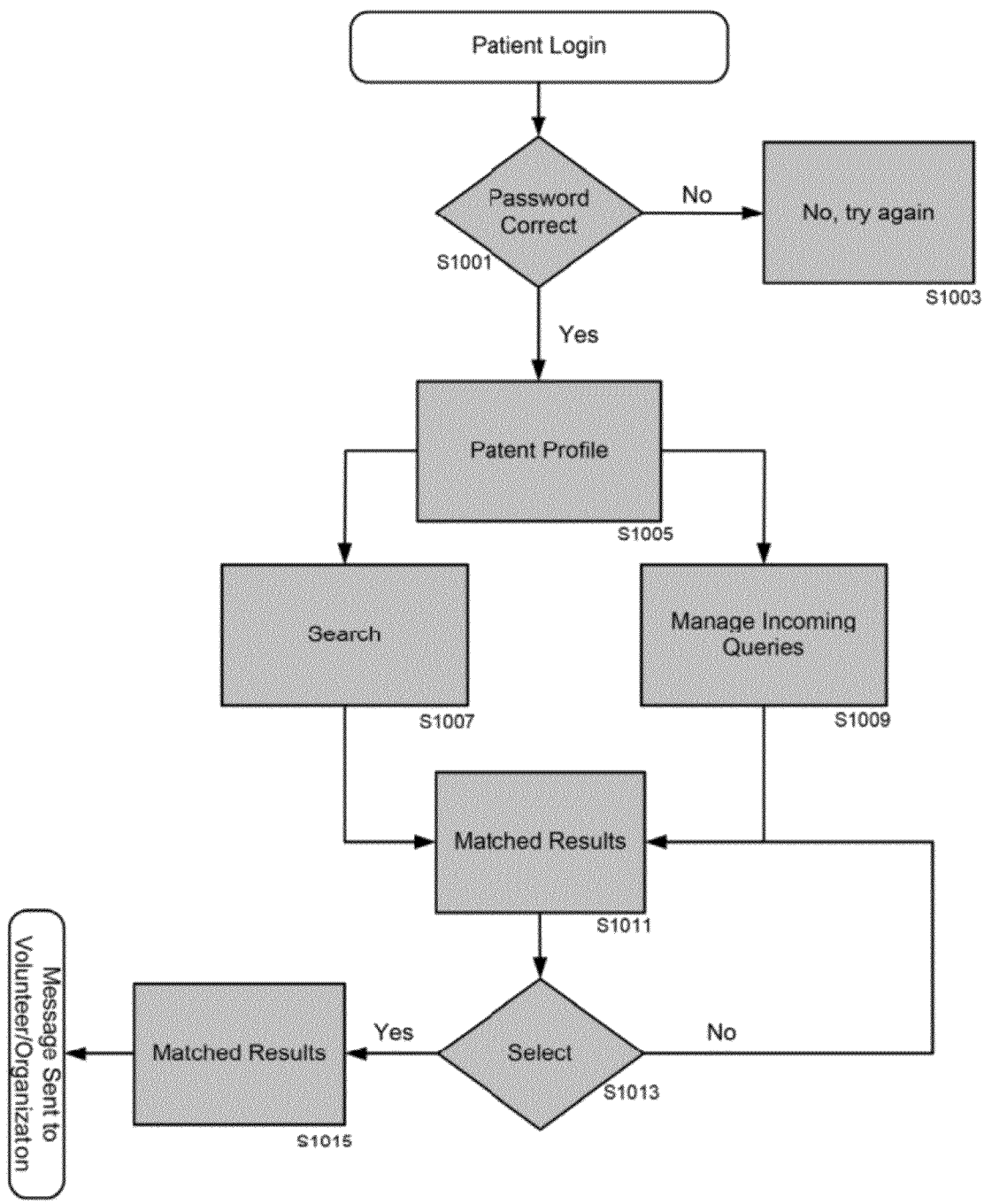
FIG. 10 illustrates an exemplary flowchart for a patient matchmaking process.

FIG. 10 illustrates an exemplary flowchart for a patient matching process. Upon logging (S1001) into the system, the patient (or the caseworker) can manage (S1005) the patient profile and search (S1007) for volunteers or manage (S1009) incoming inquiries from volunteers looking to help the patient. Similar to the interface provided to the volunteer for seeking out projects, one embodiment provides the patient with a visual display of nearby volunteers matching the patient's search criteria. Searching can optionally include using a mapping system (e.g. GIS) to identify volunteers within a certain area. Based on the patient's search or corresponding to a volunteer inquiry (S1011), the patient can select (S1013) whether to communicate with a volunteer. If the patient selects to communicate (S1015) with a volunteer, an email or internal message is sent to the selected volunteer to arrange for pro bono medical services. In one embodiment, the volunteer can refer the patient request to another or an additional volunteer on the system if, for example, the patient requires a different specialist or an additional specialist, respectively. Another embodiment integrates a medical questionnaire relating to the patient's symptoms (e.g. through integration with free online sources such as WebMD) to recommend a type of specialist volunteer to the patient. In another embodiment, a direct communication link such as VoIP, webcam, video conference or Cisco HealthPresence™ is provided between the matched patient and the volunteer to facilitate remote diagnosis and/or treatment. Pro bono patients can be provided treatment in a rural setting using this direct communication line. In addition, monitoring devices such as radiography, x-rays, MRI scans, vital signs, remote monitoring devices and other diagnostic patient data can be uploaded via the direct link to provide the patient diagnosis and/or treatment. In one embodiment, this data is securely stored on the system and retrieved and updated with secure-access compatible devices.

In one embodiment, the system provides a networked platform for rapid initiation and coordination of volunteer emergency response efforts to a public health event. Emergency response efforts may be triggered by one of a variety of natural and man-made public health events, including floods, fires, earthquakes, hurricanes, tornados, industrial accidents, bioterrorism and conventional terrorist attacks. In the context of such disasters, organizations and volunteers often are willing to assist. In one embodiment, organizations create project profiles on the system corresponding to their emergency relief efforts in the manner described previously.

In another example, the system generates requests for assistance from volunteers, organizations and donors in response to a system alert corresponding to a particular emergency. The system alert may be triggered by a system administrator or a qualified volunteer or qualified organization. Alternatively, the system alert can be triggered by receipt of an emergency assistance request signal from a public safety or law enforcement systems. For example, a federal or state entity such as FEMA or the governor's office can declare a state of emergency, thereby sending out electronic alerts. Volunteers are able to opt-in or opt-out to be alerted to such emergency response opportunities. In yet another embodiment, the system provides for location- and situation-based coordination of volunteer emergency response efforts. In this embodiment, the system receives, over a secure connection, E-911 data from a public agency such as a Public Service Access Point (PSAP) or 911 call center to identify the approximate location of one or more persons in need of emergency medical assistance. The E-911 data can also include information describing the nature of the emergency (e.g. multi-car accident, chemical spill, tornado strike) and the reported or estimated number of victims. The system then transmits a request for assistance (for example, a text message or email) to one or more qualified volunteers within a predetermined proximity to the reported injured persons. In one embodiment, the volunteer's position information is transmitted to the system so the system can monitor the whereabouts of individual volunteers. In this manner, the closest qualified volunteers can be contacted. In another embodiment, the system can use an algorithm to connect volunteers with receiving centers (RCs), which are pre-signed locations specified by organizations as a location for emergency medical services. In one embodiment, qualified volunteers include those volunteers who have opted into the emergency response feature and have profiles denoting experience in emergency medicine or trauma. If the accident involves a toxic material spill, for example, qualified volunteers might include those with profiles denoting experience handling hazardous materials or dealing with chemical burns.

Figure 11:
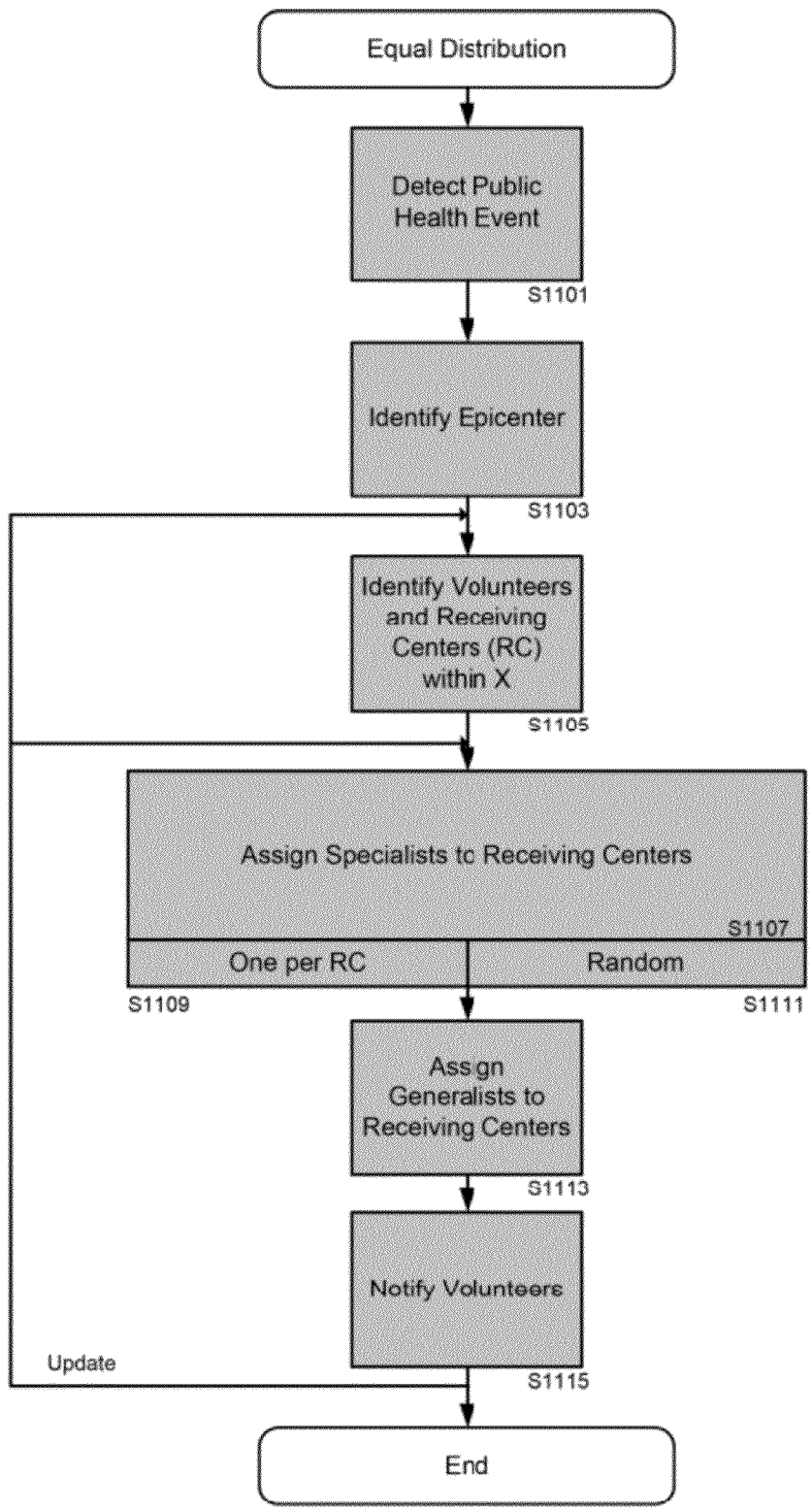
FIG. 11 illustrates an exemplary flowchart for a dynamic location-based coordination of volunteers using an equal distribution.
Figure 12A:
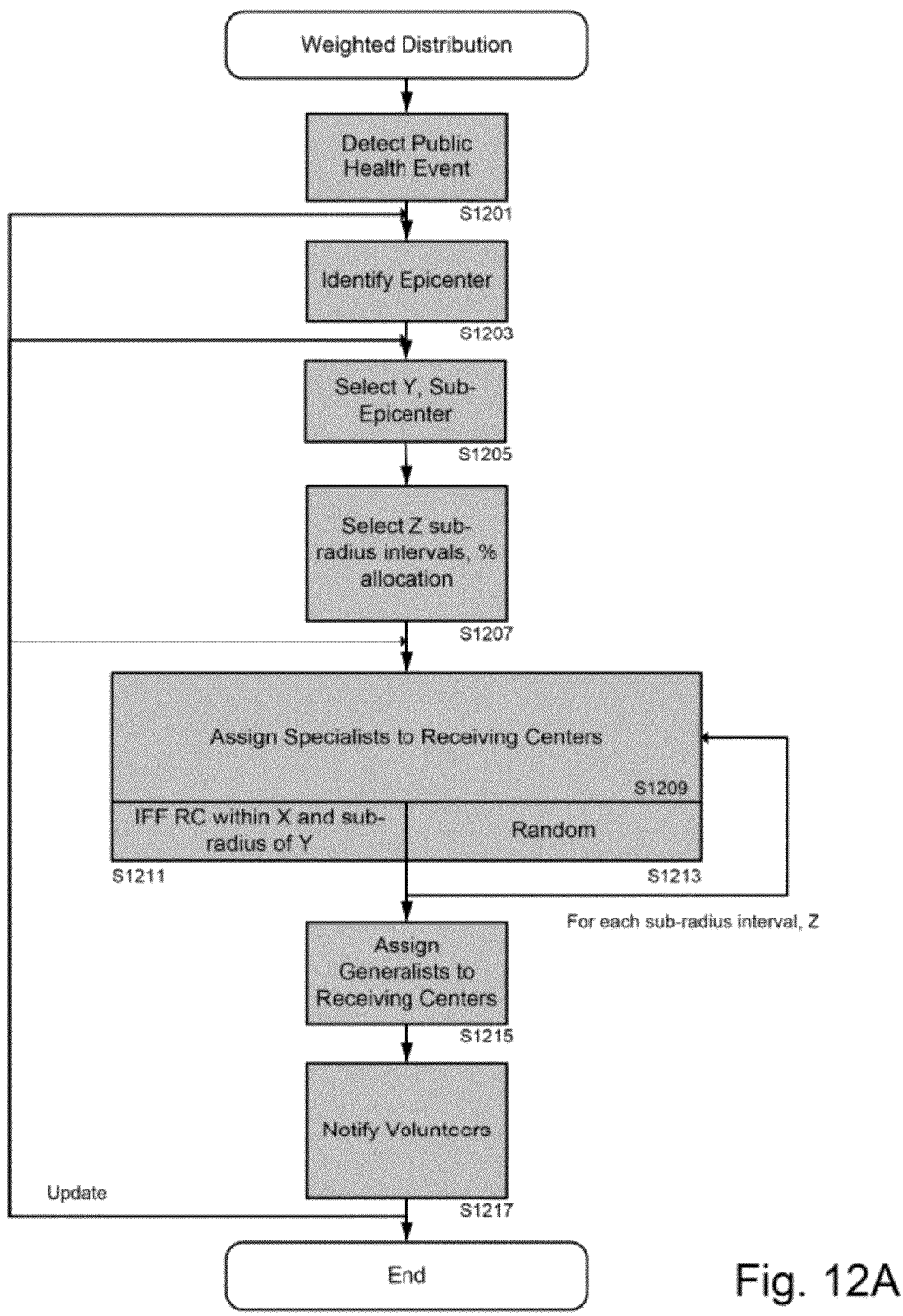
FIG. 12A illustrates an exemplary flowchart for a dynamic location-based coordination of volunteers using a weighted distribution.
Figure 12B:
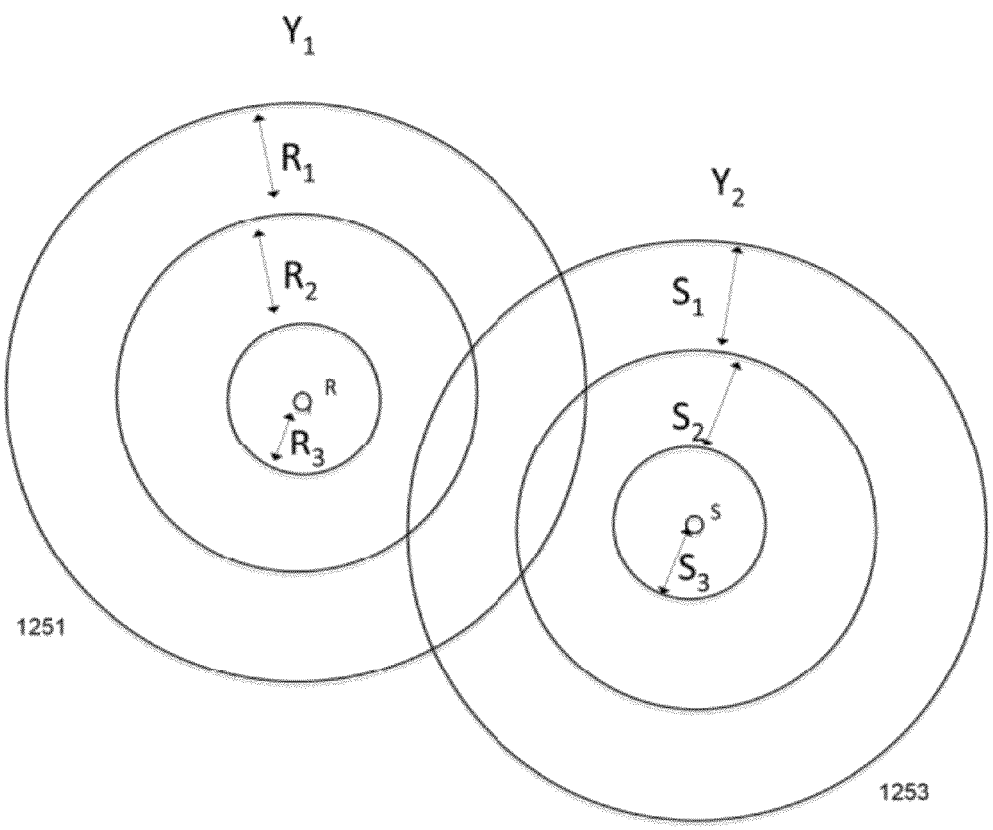
FIG. 12B is a schematic representation of multiple sub-epicenters.

FIGS. 11-12B illustrate exemplary methods for dynamic location-based coordination of volunteers, forming a public health aid network. Such methods are applicable in the traditional volunteering model, as well as in emergency response scenarios. FIG. 11 illustrates an exemplary flowchart for a dynamic location-based coordination of volunteers using an equal distribution. Initially, the system receives an indication of a public health event triggered, for example, by a system alert as described above (S1101). Next, an epicenter of the public health event is identified (S1103). The epicenter location can be indicative of a variety of conditions relative to effective response to a public health event, including identifying the location of an explosion, the center-most point of a devastated area or highest concentration of reported infections, the area of an initial onset of the event (e.g. the starting point of a communicable epidemic), or the largest area of widespread damage or destruction. Identification can be accomplished by a variety of suitable means, including without limitation identification of a specific lat-long by a system administrator, volunteer or organization, as well as receiving input from emergency response agencies or teams with location data identifying the geographical location of one or more public health event epicenters. In one embodiment, the epicenter is declared based on information received from a public safety agency (e.g. a street address, latitude/longitude ("lat/long") or GPS coordinates, neighborhood or other location-identifier where emergency response teams are being sent). In another embodiment, the epicenter is estimated based on a number of mobile emergency calls or beacons activated in a certain area and reported to a public safety agency or other entity. In another embodiment, location information associated with status messages and updates by system users can be used to estimate the location of the emergency, with the effective center-of-mass of these messages being designated as an epicenter. In yet another embodiment, the epicenter is calculated by the system based upon borders outlining the affected region that are entered by a system administrator or other user using a graphical interface displaying a map of the relevant area. In such an embodiment, the borders can be created as a line or group of coordinates in any shape to represent a regional epicenter or epicentral area, as opposed to a single geographical point. Status messages and updates may be posted internally on the system and posted using the internal messaging service, or through user-permitted interfaces with user's social networking accounts, such as Facebook and Twitter.

The system then identifies the number of specialist and generalist volunteers, n, in the local area (e.g. metropolitan statistical area (MSA)) of the public health event and the number of receiving centers (RCs), T, within a predetermined distance (e.g. X miles) from the epicenter, or within a non-circular affected region that includes the epicenter (S1105). In one embodiment, n reflects the number of volunteers within the area defined by radius X. In another embodiment, n represents the number of volunteers who have indicated their preference or ability to report to a receiving center within the region defined by X in a public health event. Receiving centers, which are pre-designated clinical centers or locations specified by organizations as locations for emergency medical services include without limitation hospitals and clinics, as well as triage and trauma surgery centers set up by emergency response teams. The response radius, X, or the affected region can be input by an administrator and updated. In one embodiment, the response radius or affected region is updated automatically depending on the severity of public health event, available emergency and volunteer resources, required resource amounts and travel distances.

Within the response radius, X, there would generally be n/T volunteers per receiving center for the system to assign (S1107). In this equal distribution embodiment, the system proceeds by, for each required or desired specialty, i) assigning one volunteer specialist per RC (S1109); or ii) randomly allocating specialist to the various RCs (S1111). If there are more volunteers of a particular specialty than RCs in the radius X, then the specialists are distributed evenly across the RCs, with the balance being distributed randomly. In one embodiment, if there are not enough specialists for each RC to get one (or when dealing with the balance of the specialists where $n_{specialty}$>T), then specialists are assigned in so that the greatest amount of distance is achieved by placing the specialists in that array of receiving centers. Every permutation of specialists is attempted and then the resulting total aggregate sum of distances between each of the specialists to each other is calculated to decide the best distribution.

For example, given the task of assigning two specialists of a given type (n=2) and three possible RCs (r=3), A, B and C, the system calculates the distances between assigned specialists (given the locations of the respective RCs) for the three possible scenarios (e.g. the two volunteers being assigned to A and B, B and C, A and C). The system then chooses the assignment that results in the greatest distance between RCs or assigned volunteers. For example, if the distance from A to B is 2 miles, from A to C is 10 miles and from B to C is 9 miles, then volunteers are assigned to RCs A and C, as that assignment maximizes the distance between RCs with volunteers. The system then assigns generalists (non-clinicians, non-specialists) (S1113). Again, if there are more generalists than RCs, then they are distributed similar to the method described above with respect to specialists. If there are fewer generalists than RCs (or for the balance remaining after equal distribution), then they can be assigned to maximize the distance between the remaining generalists.

FIG. 12A illustrates an exemplary flowchart for a dynamic location-based coordination of volunteers using a weighted distribution. Initially, the system receives an indication of a public health event triggered, for example, by a system alert (S1201). Next, an epicenter of the public health event is identified (S1203). A system administrator, qualified volunteer or qualified organization can then designate Y (e.g. using lat/long, address, etc.) as a sub-epicenter (S1205). Optionally, sub-epicenter Y may be the same as the epicenter determined using the approaches described previously.

The system then receives inputs defining a number of sub-intervals, Z, from the sub-epicenter Y and a desired or target allocation of volunteers to fall within each sub-intervals (S1207). Sub-intervals can be defined by a variety of factors, including without limitation estimates on where victims are most likely located, a location of greatest number of probable victims, food shortages, hospital status, human-processed decisions from messages sent from victims on the ground to the system or system administrator, closed roadways, rail track closures, airport closures and other blockages. For example, in one embodiment, the sub-interval 0-1 miles from sub-epicenter Y would get A % of n available specialist or generalist volunteers, the sub-interval between 1-2 miles from sub-epicenter Y would get B % of available volunteers, the sub-interval between 2-3 miles from sub-epicenter Y would get C % of the n volunteers, and the sub-interval 3 miles and out from sub-epicenter Y would get D % of the n volunteers. In one embodiment, A=40%, B=30% C=20%, D=10%. Z can be calculated by set interval or graded interval or set manually. Generally, for an allotment of volunteers for any one sub-epicenter, the percentage allocation would add up to 100% so all volunteers are assigned somewhere.

Next, for each sub-interval, the system assigns specialists to RCs (S1209). In this weighted distribution embodiment, the system proceeds by, for each required or desired specialty, i) assigning one volunteer specialist per RC if and only if (iff) the RC is within the sub-radius region of Y (which is NOT within the next smallest radius) AND within the radius X (S1211); or ii) randomly allocating specialist to the various RCs (S1213). If there are more volunteers of a particular specialty than RCs in the sub-radius, then the specialists are distributed evenly across the RCs in that sub-radius, with the balance being distributed randomly.

If there are more volunteers of a particular specialty than RCs in a particular sub-radius, then the specialists are distributed evenly across the RCs, with the balance being distributed randomly or more heavily weighted in areas where two sub-epicenter radii coincide or overlap (the union of the radii). In one embodiment, if there are not enough specialists for each RC to get one (or when dealing with the balance of the specialists where $n_{specialty}$>T), then specialists are assigned in so that the greatest amount of distance is achieved by placing the specialists in that array of RCs. Every permutation of specialists is attempted and then the resulting total aggregate sum of distances between each of the specialists to each other is calculated to decide the best distribution. The system then assigns generalists (non-clinicians, non-specialists) (S1213). Again, if there are more generalists than RCs, then they are distributed similar to the method described above with respect to specialists. If there are fewer generalists than RCs (or for the balance remaining after equal distribution), then they can be assigned to maximize the distance between the remaining generalists.

FIG. 12B is a schematic representation of multiple sub-epicenters. Accounting for more than one sub-epicenter, individual and groups of volunteers (generalists and specialists) can be assigned to one of several sub-epicenters. In one embodiment, multiple sub-epicenters are identified so one or more groups of volunteers are assigned to a specific sub-epicenter and distributed among sub-intervals. In the illustrated example, there are two sub-epicenters, R and S defining affected regions $Y_1$ 1251 and $Y_2$ 1253, respectively. Affected regions $Y_1$ and $Y_2$ correspond to n total volunteers. Region $Y_1$ includes sub-intervals $R_1$, $R_2$ and $R_3$. Region $Y_2$ includes sub-intervals $S_1$, $S_2$ and $S_3$. In the illustrated example, if region $Y_1$ 1251 is deemed to be more severely impacted than region $Y_2$ 1253, then more volunteers may be allocated to region $Y_1$ 1251. If the total number of volunteers, n, is 200, then 140 volunteers may be allocated to region $Y_1$ and the remaining 60 may be allocated to region $Y_2$. The desired intra-interval concentrations of volunteers are then input. In one embodiment, these are set by a system administrator, relief organization or other qualified user. In another embodiment, they are set automatically according to a gradient corresponding to published best practices for emergency responses to various public health events. For example, $R_1$ and $S_1$ may be set to 20% of the region's total allocation of volunteers, $R_2$ and $S_2$ may be set to 30% and $R_3$ and $S_3$ may be set to 50%. $R_n$ and $S_n$ can be set to any suitable allocation. Thus, in this specific example, $R_3$ would have 70 assigned volunteers, $R_2$ would have 42 volunteers, $R_1$ would have 28 volunteers, $S_3$ would have 30 volunteers, $S_2$ would have 18 volunteers and $S_1$ would have 12 volunteers. The volunteers are then allocated to RCs within each of the sub-intervals. In one embodiment, the equal distribution dynamic coordination method is applied to assign the allotted volunteers in each sub-interval to RCs therein. In another embodiment, the weighted distribution dynamic coordination method is applied. In another embodiment, a combination of these dynamic coordination methods is applied.

Volunteers can be notified of their assignments, updated assignments and other messages using a variety of communications methods. For example, these include voice messages transmitted to landline or mobile telephones. These also include text, email, ham/shortwave radio frequencies, Morse code, walkie-talkie frequencies and other means (e.g. a notification sent to an application running locally on a network-connected mobile or desktop device). In one embodiment, volunteers can opt out of receiving real-time updates or designate a desired interval for updates. With volunteers' consent, their location can be tracked using GPS or other technology in real-time to enhance the efficiency of the volunteer assignments and real-time reassignments of volunteers. Messages can also be disseminated to certain receiving centers. In one embodiment, victims, available food, equipment and supplies area also identified and tracked in real-time.

In one embodiment, a system administrator chooses the frequency of updates as the number and types of specialists changes. This may cause some specialists to be reassigned to a different RC, where the cost/benefit of reallocating specialists is weighed against having them spread equally out along the epicenter of the public health event. In one embodiment, based on a message sent from the volunteer, a system administrator, RC or a predetermined time interval, the system applies a dynamic coordination method to relieve certain volunteers with back-up volunteers of the same or similar specialty. In another embodiment, the system receives or calculates indications of fatigue or under/overstaffing to trigger a dynamic coordination method to replace tired or add additional volunteers with the same or similar specialty.

In a major public health event such as a terrorist attack or a hurricane, mobile communications may be compromised or hampered. In view of these situations, an embodiment of the system detects communication network failures, for example, by failed calls or texts to volunteer mobile numbers or by coordination with mobile or land-based Internet providers to identify service outages. In one embodiment, during times prior to a communications network outage (e.g. prior to the public health event), the system notifies volunteers of their assigned emergency receiving center(s) for a given location (e.g. the volunteer's stated work location, stated home location, or "roaming range" determined by monitoring and evaluating location data submitted with consent by the volunteer over a period of time) at predetermined intervals. The assigned receiving centers can be determined and updated, for example, by one of the dynamic coordination methods described above. By notifying the volunteer prior to the emergency, the system provides volunteers with a starting point for reporting to a particular receiving center during a public health event. One embodiment works around mobile communication failures by attempting to contact and update volunteers using landline numbers identified in the volunteer profiles. Further, another embodiment transmits updates to the receiving centers, which may rely on more robust communications channels reserved or enabled for emergency response entities in case of emergency, to provide updates on which volunteers should reallocate and which should remain in their current position. Yet another embodiment provides a log of sent alerts and updates so a volunteer or organization can review these messages once their communication abilities are restored.

Figure 13:
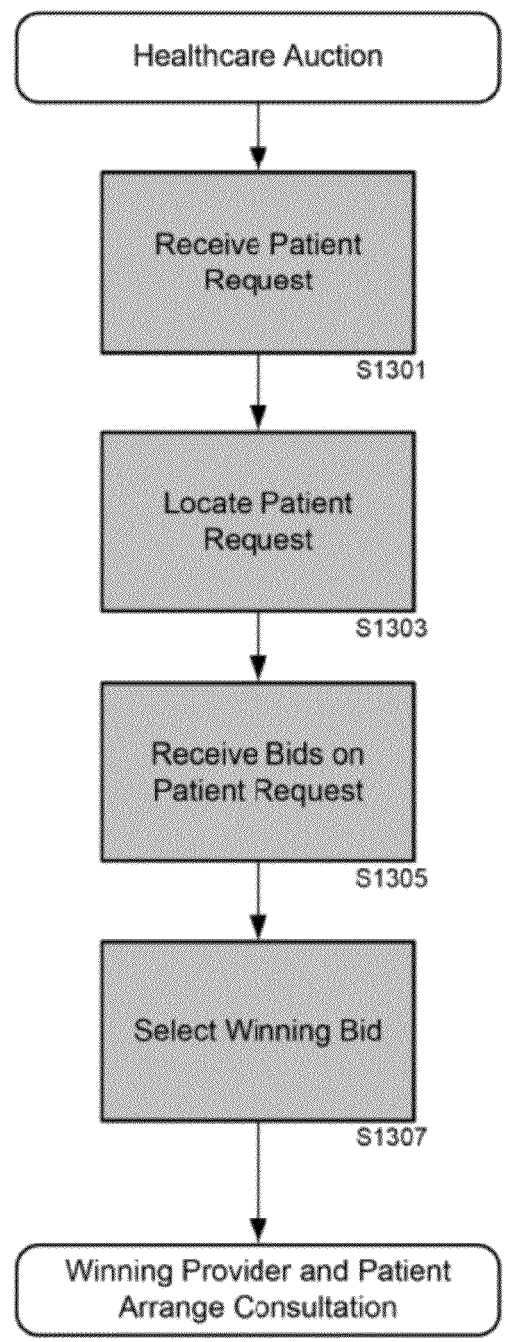
FIG. 13 illustrates an exemplary flowchart for a healthcare auction embodiment of the system.

FIG. 13 illustrates an exemplary flowchart for a healthcare auction embodiment of the system. Initially, the system receives a patient (or case worker) request for free or reduced-cost healthcare (S1301). In one embodiment, the patient's request includes a description of the symptoms and/or requested specialist. In another embodiment, indications of the patient's identity (e.g. name, address) are blocked to preserve privacy, while other indications (e.g. age, gender, symptoms) may be revealed to a volunteer with sufficient security credentials to view sensitive patient data. Using the system, a volunteer, such as a specialist, or organization locates and accesses a patient request through, for example, a keyword search or other health condition identifying criteria (S1303). The system then receives a bid from one or more volunteers (S1305) for a predetermined time period (e.g. an auction lasting for a predetermined amount of time, number of received bids, bids reading $0, acceptance by the patient). The patient then reviews the received bids and a winning bidder is selected (S1307). Selection may be accomplished by choosing the lowest bid during the auction period, or may be indicated by the patient (e.g. the patient selects a "winning bid" before the auction time expires. Once the auction is ended, the system sends a secure message to one of (or both) the patient and the volunteer so they can arrange for services to be provided. An auction format advantageously provides an opportunity to extend the healthcare volunteer model, broaden the scope of potential volunteers to include providers needing or desiring at least some remuneration for their services, thereby further serving the uninsured and the underinsured.

Various embodiments of the system provide security measures to ensure patient privacy and data security, such as the handling of medical information and electronic health records (EHR). For example, patient medical information is stored securely (e.g. password/authentication-protected, encrypted) on the system and accessible only by the patient and parties explicitly permitted by the patient. Permitted parties may include healthcare providers (e.g. a treating physician). For example, the security measures may include fingerprint or retina verification, security questions and passwords. The measures may also include blacking out patient names and other information, warping or obscuring images of patients. One embodiment includes credential verification, including checking online public and private database to grant access to only certain health providers, where the databases include federal, state and international databases for license status, pharmacy/DEA/controlled substance licenses, malpractice insurance company certificate of insurance filings, credentialing and certifying agencies, medical specialty Board databases and insurance company associations. Methods for transfer of sensitive patient data are also employed, such as password-protection, encryption, anonymization and decoupling or coding of patient medical and identification information. In another embodiment, HIPAA and other relevant requirements are met by incorporating electronic consent forms to obtain patient consent for sharing patient data with certain relevant parties, as well as allowing for electronic revocation of previously given consent. Embodiments of the system accommodate security measures in compliance with applicable federal requirements such as standards for Certified EHR Technology and output or presentation of clinical information to patients in a "human readable format." Additionally, embodiments of the system include interfaces with various electronic health records systems for secure and accurate sharing of patient medical data, such as over the National Electronic Health Information Network. Embodiments of the system can also receive updates from various third-party systems, including updates from the Regional Extension Center (REC) and state Medicaid systems. Other interfaces include those to electronic prescription fulfillment tracking systems, tobacco smoking cessation databases, immunization registries and allergy and contraindication update lists.

Figure 14:
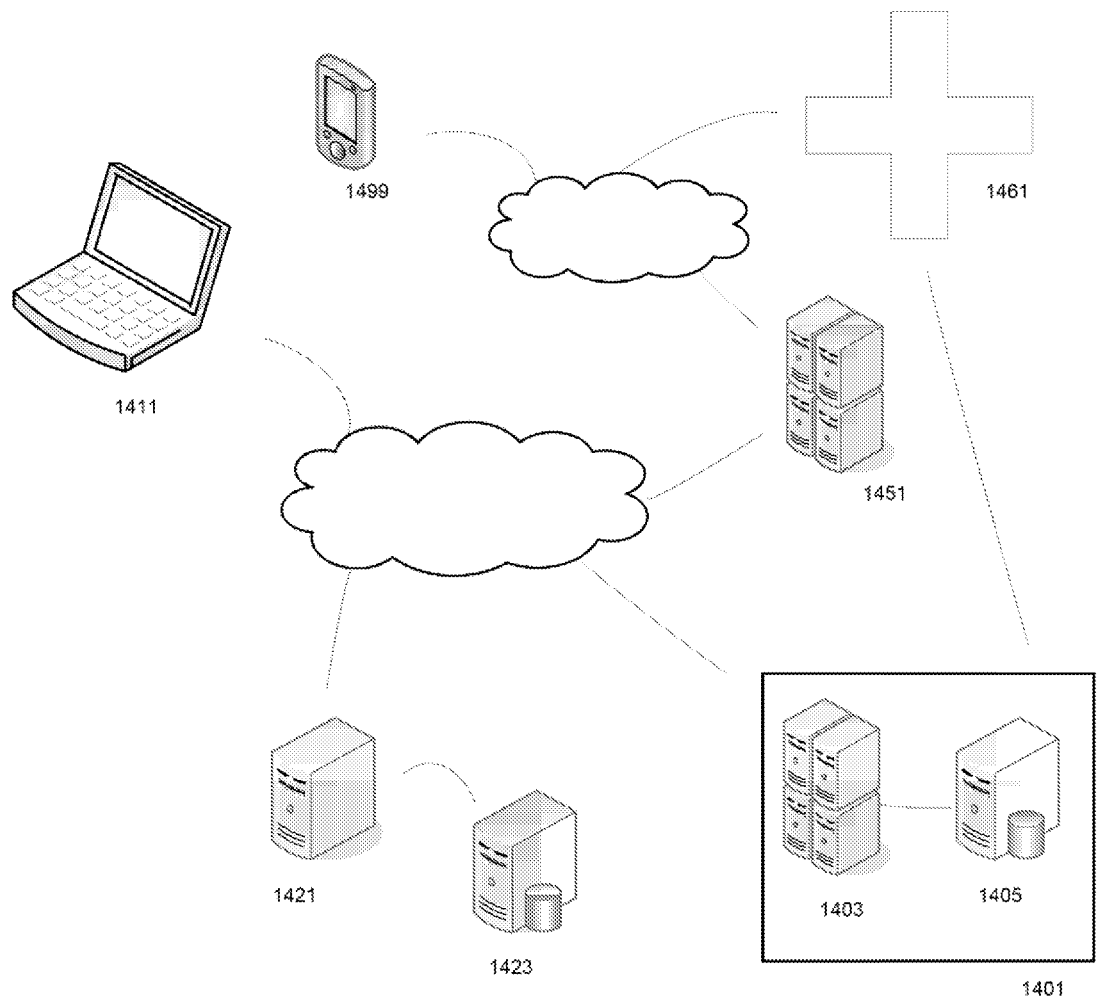
FIG. 14 illustrates an exemplary system for performing these processes.

FIG. 14 is a schematic diagram of an embodiment of the system. The system 1401 includes a webserver 1403 and a system database 1405. The system 1401 further includes a messaging system and an email server allowing the various users to be notified of activity on the system (e.g. potential volunteer-project matches, potential available inventory) and to communicate with each others. The system database 1405 stores information relating to the various users and projects, including volunteer profiles, organization profiles, patient profiles, donor profiles, inventory data, and messaging data. Users, including volunteers, organizations, case workers, patients, and various donors, connect to the system 1401 through a wired or wireless Internet connection using a volunteer client 1411 (e.g. a desktop, netbook or laptop) or a mobile device 1499, such as a mobile phone, PDA, smart phone (e.g. iPhone, Android-enabled phone, BlackBerry) or tablet (e.g. iPad, Playbook). The system 1401 also interfaces with mobile data/voice providers through a gateway server 1451 to transmit and receive messages/data from the system 1401 over mobile networks to users of SMS-enabled and mobile-Internet-enabled devices such as 2G-, 3G- and 4G-enabled mobile phones. For example, the system can transmit SMS or Internet-based (e.g. using an application running on a mobile Internet-enabled phone) alerts to mobile devices regarding volunteering opportunities, and the system can receive location information from the mobile device (e.g. GPS-enabled handsets) or from a mobile service provider. In another embodiment, the system interfaces with PSAPs or other government entities 1461 to provide the requisite data exchange (e.g. volunteer handset locations, emergency response team communications and requests) to coordinate disaster response efforts.

In one embodiment, an organization can opt to directly connect their corporate computing system 1421, including their project database and/or inventory database 1423 for real-time or periodic syncing with the information stored on the system database 1405. For example, a donor organization can connect its corporate inventory system (or a subset or mirror thereof) to the healthcare volunteer system 1401 by transmitting an XML feed, RSS or other structured data format to the system database 1405 at predetermined intervals, manually or upon any update to the corporate inventory system. Alternatively, the system 1401 can initiate the update process and access an updated inventory file made available by the organization's system 1421 at, for example, a predetermined secure URL or network communication port.

The various disclosed embodiments advantageously facilitate communication and coordination among healthcare volunteers, organizations, patients and donors.

While the foregoing description includes many details and specificities, it is to be understood that these have been included for purposes of explanation only, and are not to be interpreted as limitations of the present invention. It will be apparent to those skilled in the art that other modifications to the embodiments described above can be made without departing from the spirit and scope of the invention. Accordingly, such modifications are considered within the scope of the invention as intended to be encompassed by the claims set forth below.

The invention claimed is:

1. A computer-implemented method for coordinating a response of volunteers, including specialist volunteers and generalist volunteers, to a public health event, comprising:
   receiving, on a network-accessible computer, data indicative of a public health event;
   identifying a location of an epicenter of the public health event and storing the location in a memory of the computer;
   identifying, in response to the public health event, volunteers and receiving centers within a predetermined distance of the epicenter using a processor, wherein
   identifying volunteers includes: (i) receiving volunteer and location data reflecting a volunteer position, the volunteer position comprising a current position of a volunteer or a position to which the volunteer has indicated an ability to report and determining a distances between the volunteer position and the location of the epicenter, and (ii) computing a number of volunteers for which the distance between the volunteer position and the location of the epicenter is less than or equal to a preselected threshold distance, and
   identifying receiving centers includes: (i) determining distances between stored receiving center locations and the location of the epicenter, and (ii) computing a number of center locations for which the distance between the stored receiving center location and the location of the epicenter is less than or equal to the preselected threshold distance;
   designating as a set of volunteers either, (i) the identified volunteers when the computed number of volunteers is less than the computed number of receiving centers, or otherwise (ii) a balance of volunteers in excess of those that can be assigned uniformly to the receiving centers;
   assigning, using a processor, volunteers to receiving centers within the predetermined distance of the epicenter, the assigning step comprising identifying a first, a second, and a third receiving center, such that a distance between the first and second receiving centers is greater than a distance between the first and third receiving centers, assigning from the designated set at least one volunteer to each of the first and second receiving centers, and assigning no volunteers to the third receiving center;
   transmitting, using a transmitter connected to the network, notifications to the specialist volunteers and generalist volunteers of their respective assignments.

2. The computer-implemented method of claim 1, wherein assigning specialist volunteers to receiving centers within the predetermined distance of the epicenter includes:
   computing a ratio obtained by dividing the computed number of volunteers by the computed number of receiving centers;
   assigning at least volunteers specified by the computed ratio to each receiving center; and
   randomly assigning remaining volunteers to the receiving centers.

3. The computer-implemented method of claim 1, further comprising:
   identifying, using a processor, sub-intervals within the predetermined distance of the epicenter and respective target number of specialist volunteers and generalist volunteers for each sub-interval, wherein assigning specialist volunteers to receiving centers within the predetermined distance of the epicenter includes:
   assigning at least one specialist to each receiving center if the receiving center is located within the sub-interval and within the predetermined distance from the epicenter, or
   randomly assigning specialist volunteers to receiving centers.

4. The computer-implemented method of claim 3, further comprising:
   identifying a second location of a second epicenter and storing the second location in the memory of the computer, the first and second epicenter defining overlapping regions; and
   assigning, using a processor, left-over specialist volunteers to receiving centers in corresponding sub-intervals.

5. The computer-implemented method of claim 1, further comprising:
   identifying, using a processor, one of a victim, food and supplies; and
   reflecting and storing within a memory of the computer a real-time position of one of the victim, food and supplies.

* * * * *

UNITED STATES PATENT AND TRADEMARK OFFICE
CERTIFICATE OF CORRECTION

PATENT NO. : 8,548,839 B2  Page 1 of 1
APPLICATION NO. : 12/945569
DATED : October 1, 2013
INVENTOR(S) : Patel It is certified that error appears in the above-identified patent and that said Letters Patent is hereby corrected as shown below:

On the Title page Item [12], delete "Neilesh" and insert --Patel--

On the Title page Item [75] Inventor, delete "Patel Neilesh" and insert --Neilesh Shashikant Patel--

Signed and Sealed this
Twenty-sixth Day of November, 2013

Margaret A. Focarino
*Commissioner for Patents of the United States Patent and Trademark Office*